(12) United States Patent
Jarman et al.

(10) Patent No.: US 6,487,523 B2
(45) Date of Patent: Nov. 26, 2002

(54) MODEL FOR SPECTRAL AND CHROMATOGRAPHIC DATA

(75) Inventors: Kristin Jarman, Richland, WA (US); Alan Willse, Richland, WA (US); Karen Wahl, Richland, WA (US); Jon Wahl, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 09/866,201

(22) Filed: May 25, 2001

(65) Prior Publication Data

US 2002/0035449 A1 Mar. 21, 2002

Related U.S. Application Data

(63) Continuation-in-part of application No. 09/288,758, filed on Apr. 7, 1999, now Pat. No. 6,253,162, and a continuation-in-part of application No. 09/765,872, filed on Jan. 19, 2001, now Pat. No. 6,366,870.

(51) Int. Cl.[7] ............................ G06F 19/00; B01D 59/44
(52) U.S. Cl. ......................... 702/189; 250/281; 250/282; 702/28; 702/181
(58) Field of Search ............................ 702/189, 22, 23, 702/24, 25, 27, 28, 181; 356/300; 250/281, 282

(56) References Cited

U.S. PATENT DOCUMENTS

| | | | |
|---|---|---|---|
| 6,253,162 B1 | * | 6/2001 | Jarman et al. .............. 250/282 |
| 6,366,870 B2 | * | 4/2002 | Jarman et al. .............. 250/282 |

OTHER PUBLICATIONS

A. Nijhuis et al., "Multivariate statistical process control in chromatography", *Chemometrics and Intelligent Laboratory Systems* v. 38, pp. 51–62 (Elsevier Science B.V. 1997).

Arnold, R. J. and Reilly, J. P., "Fingerprint Matching of E.Coli Strains with Matrix–assisted Laser Desorption/Ionization Time–of–Flight Mass Spectrometry of Whole Cells Using a Modified Correlation Approach", *Rapid Communications in Mass Spectrometry*, v. 12, pp. 630–636 (1998).

Martens, H. and Naes, T., "Multivariate Calibration", pp. 85–101 (John Wiley & Sons).

* cited by examiner

*Primary Examiner*—Patrick Assouad
(74) *Attorney, Agent, or Firm*—Woodard, Emhardt, Naughton, Moriarty & McNett

(57) ABSTRACT

A method and apparatus using a spectral analysis technique are disclosed. In one form of the invention, probabilities are selected to characterize the presence (and in another form, also a quantification of a characteristic) of peaks in an indexed data set for samples that match a reference species, and other probabilities are selected for samples that do not match the reference species. An indexed data set is acquired for a sample, and a determination is made according to techniques exemplified herein as to whether the sample matches or does not match the reference species. When quantification of peak characteristics is undertaken, the model is appropriately expanded, and the analysis accounts for the characteristic model and data. Further techniques are provided to apply the methods and apparatuses to process control, cluster analysis, hypothesis testing, analysis of variance, and other procedures involving multiple comparisons of indexed data.

29 Claims, 10 Drawing Sheets

| $p_j$ | $q_j$ | N | \multicolumn{7}{c}{Specified significance level $\alpha$} |
| | | | 0.2 | 0.15 | 0.1 | 0.05 | 0.01 | 0.001 |
|---|---|---|---|---|---|---|---|---|
| $p_j = 0.9; j=1,2,...N$ | $q_j = 0.05; j=1,2,...N$ | 8 | 0.057 | 0.0058 | 0.0058 | 0.0058 | 0.0058 | 0.0004 |
| | | 10 | 0.011 | 0.011 | 0.012 | 0.012 | 0.001 | 0.001 |
| | | 12 | 0.020 | 0.020 | 0.020 | 0.020 | 0.0022 | 0.0022 |
| | | 14 | 0.030 | 0.030 | 0.030 | 0.004 | 0.004 | 0.0004 |
| | | 16 | 0.043 | 0.043 | 0.043 | 0.007 | 0.007 | 0.0009 |
| | $q_j = 0.1; j=1,2,...N$ | 8 | 0.038 | 0.038 | 0.038 | 0.005 | 0.005 | 0.0004 |
| | | 10 | 0.070 | 0.070 | 0.013 | 0.013 | 0.002 | 0.002 |
| | | 12 | 0.026 | 0.026 | 0.026 | 0.026 | 0.004 | 0.005 |
| | | 14 | 0.030 | 0.030 | 0.030 | 0.004 | 0.004 | 0.0004 |
| | | 16 | 0.043 | 0.043 | 0.043 | 0.007 | 0.007 | 0.0009 |
| $p_j = 0.9; j=1,2,...N/2, p_j=0.7; j=N/2+1,...,N$ | $q_j = 0.05; j=1,2,...N$ | 8 | 0.057 | 0.057 | 0.046 | 0.046 | 0.017 | 0.005 |
| | | 10 | 0.087 | 0.070 | 0.070 | 0.042 | 0.012 | 0.006 |
| | | 12 | 0.096 | 0.096 | 0.096 | 0.042 | 0.018 | 0.004 |
| | | 14 | 0.125 | 0.125 | 0.058 | 0.030 | 0.017 | 0.007 |
| | | 16 | 0.156 | 0.077 | 0.077 | 0.043 | 0.011 | 0.005 |
| | $q_j = 0.1; j=1,2,...N$ | 8 | 0.156 | 0.070 | 0.070 | 0.038 | 0.021 | 0.005 |
| | | 10 | 0.113 | 0.113 | 0.070 | 0.070 | 0.017 | 0.005 |
| | | 12 | 0.111 | 0.111 | 0.068 | 0.033 | 0.010 | 0.004 |
| | | 14 | 0.158 | 0.101 | 0.055 | 0.043 | 0.019 | 0.003 |
| | | 16 | 0.139 | 0.083 | 0.083 | 0.054 | 0.017 | 0.003 |

*Fig. 4*

Sample Number

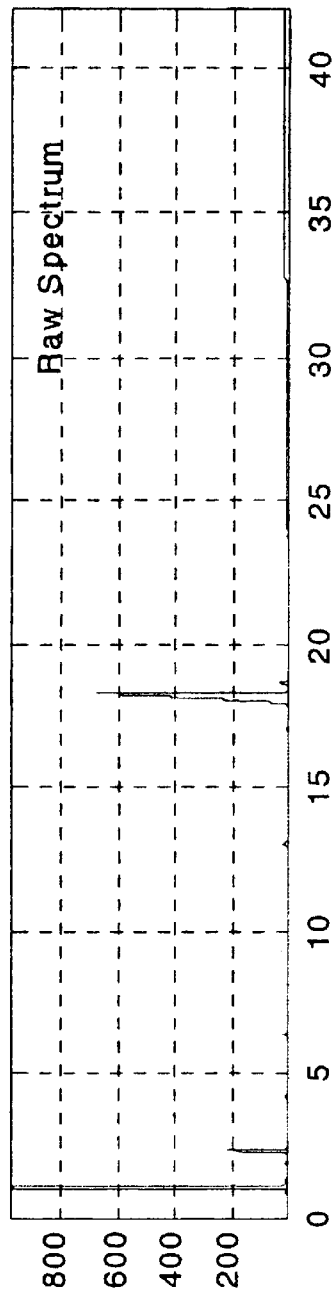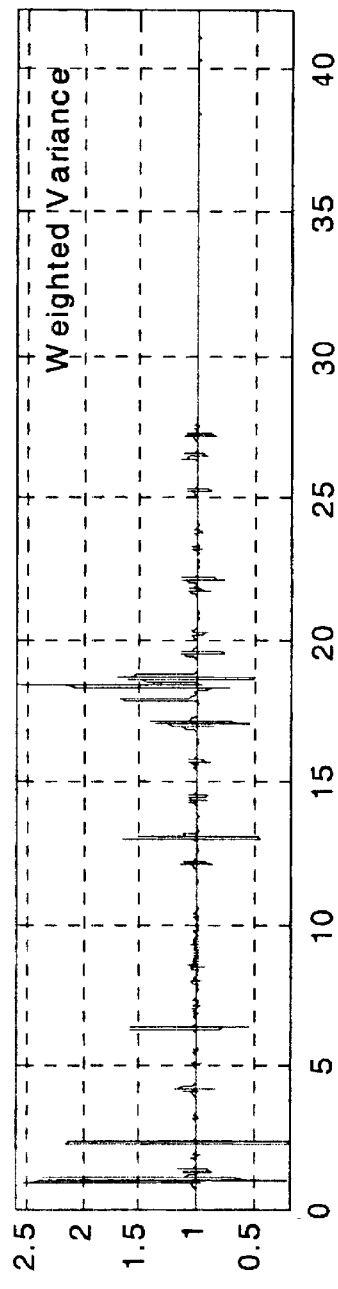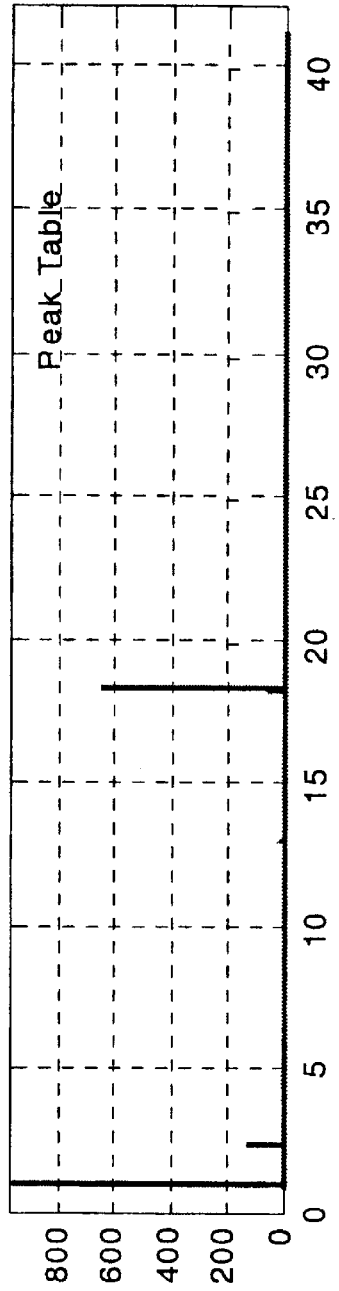
Fig. 8a (PRIOR ART)
Fig. 8b (PRIOR ART)
Fig. 8c (PRIOR ART)

MODEL FOR SPECTRAL AND CHROMATOGRAPHIC DATA

CROSS-REFERENCE TO RELATED APPLICATIONS

This is a continuation-in-part of U.S. patent application Ser. No. 09/288,758, now U.S. Pat. No. 6,253,162 filed on Apr. 7, 1999, which is entitled "Method of Identifying Features in Indexed Data," and of U.S. patent application Ser. No. 09/765,872, now U.S. Pat. No. 6,366,870 filed on Jan. 19, 2001, which is titled "Identification of Features in Indexed Data and Equipment Therefore." These documents are hereby incorporated by reference as if fully set forth herein.

This invention was made with Government support under Contract DE-AC0676RLO1830 awarded by the U.S. Department of Energy. The Government has certain rights in the invention.

FIELD OF THE INVENTION

The present invention relates generally to the evaluation of objects using spectral data, and more particularly, but not exclusively, to a method for evaluating spectrum data to determine whether samples include a particular characteristic.

BACKGROUND OF THE INVENTION

As used herein, the term "indexed data set" or "spectrum" refers to a collection of measured values ("responses") where each response is related to one or more of its neighbor elements. The relationship between the one or more neighbor elements may be, for example, categorical, spatial, or temporal. In addition, the relationship may be explicitly stated or implicitly understood from knowing the type of response data and/or how such data were obtained. When a unique index, either one-dimensional or multi-dimensional, is assigned (implicitly or explicitly) to each response, the data are considered indexed. One-dimensional indexed data is defined as data in ordered pairs (index value, response). The index values represent values of a parameter such as time, distance, frequency, or category; the response values can include but are not limited to signal intensity, particle or item counts, or concentration measurements. A multi-dimensional indexed data set or spectrum is also ordered data, but with each response indexed to a value for each dimension of a multi-dimensional array. Thus a two-dimensional index has a unique row and column address for each response (index value1, index value2, response).

Spectral/chromatographic data (as that produced by matrix-assisted laser desorption/ionization-mass spectrometry (MALDI-MS) or gas chromatography) is gathered and analyzed to characterize samples. For example, such data sets may be analyzed in an attempt to determine whether or not a known substance is present in the sample. In other applications, the data may be analyzed in an attempt to evaluate whether a chemical or biological process is performing within acceptable bounds. Some existing methods for analysis include pattern recognition techniques and visual interpretation of spectrum plots. Many techniques use principal components analysis, including partial least squares and principal component regression methods.

The identification and/or characterization of significant or useful features in the analysis of indexed data is a classic problem. Often this problem is reduced to separating the desired signal from undesired noise by, for example, identifying peaks that may be of interest. For indexed data, each of such peaks appears as a deviation, that is to say a rise and a fall (or fall and rise), in the responses over consecutive indices. However, background noise can also result in such deviations of responses leading, for example, to the identification of false peaks in indexed data.

Traditionally, peak detection has been based upon identifying responses above a threshold value. Whether this peak detection has been performed manually or by use of an automated tool, threshold selection has been a critical function that has resisted an objectively optimal solution. Thus such previously known methods for threshold selection typically require arbitrary and subjective operator/analyst-dependent decision-making and are therefore an art. The effectiveness of such artful decision-making using these known traditional methods, and peak detection as a result, is also affected by signal-to-noise ratio, signal drift, and other variations in the baseline signal. Consequently, the operator/analyst often has had to apply several thresholds to the responses over different regions of indices to capture as much signal as possible. This approach has been shown to yield results that are not reproducible, to cause substantial signal loss, and to be subject to operator/analyst uncertainty.

An example of the problems with traditional peak detection and characterization algorithms and methods is illustrated by the development of statistical analysis methods for MALDI-MS. The MALDI-MS process begins with an analyte of interest placed on a sample plate and mixed with a matrix. The matrix is a compound selected to absorb specific wavelengths of light that are emitted by a selected laser. Light from the laser is then directed at the analyte mixture causing the matrix material to become ionized. This ionization of the matrix material, in turn, ionizes some molecules of the analyte which become analyte ions 100 (FIG. 1). A charge is applied just beyond the source region to extract ions into flight tube 102 and at a detector 104 to attract analyte ions 100, where detector 104 measures the ionic charge that arrives over a time interval. This measure of charge is converted to an abundance of ions, and the measured flight time of each packet of ions is converted to a mass/charge (m/z) ratio based on flight time measurements of 2–3 known analytes. Since ions 100 arrive at detector 104 in a dispersed packet that spans multiple sampling intervals, ions 100 are binned and counted over several m/z units as illustrated in FIG. 2.

Currently used algorithms require an operator/analyst to specify a detection threshold 200 for the intensities observed so that only peaks 202 that exceed this specified threshold will be detected and characterized. This procedure for setting the detection threshold appears conceptually appealing and suggests that m/z values for which no ions are present will be read as having a baseline relative abundance, while m/z values for which ions are present will result in a peak. However, as a result of this procedure, peaks 202 that are detected for a specific analyte are not only dependent on the MALDI-MS instrument used but also on the skill of the operator/analyst in setting the detection threshold 200 used for the analysis. If such a user-defined threshold 200 is too low, noise might erroneously be characterized as a peak; whereas if threshold 200 is too high, small peaks might erroneously be ignored as noise. Thus the manual setting of detection threshold 200 introduces variability that makes accurate statistical characterization of MALDI-MS spectra difficult. In addition, baseline noise is not constant over the entire data collection window and such variability decreases even further the effectiveness of current peak detection algorithms based on baseline thresholding. Also related to the problem of distinguishing signals from noise is the bounding uncertainty of the signal. It is well known that replicate analyses of a given sample often produce slightly different indexed data due to instrument variability and other factors not tied to an operator/analyst.

The related disclosures cited above provide improved methods of identifying significant features of test spectra. There remains, however, a need for improved methods of testing samples using peak indices and characteristics that are discovered using such techniques. Such applications include qualitative analysis (wherein one attempts to determine whether a sample does or does not contain a particular substance) and process control (wherein one attempts to detect at what point in time a process degrades to an unacceptable state).

The goal of process control in this context is to take sample spectra at given time epochs, and based on those spectra, to determine when the process begins to degrade or fail (i.e., becomes "out of control"). Several techniques have been developed for control of analytical processes. Many of these methods take a series of sample spectra and compare each to the statistical distribution of a reference spectrum to determine if that spectrum falls inside or outside the expected range of variation for an under-control process. Such methods are useful for identifying dramatic changes in a monitored process, but they are generally deficient when processes undergo gradual or subtle changes over time.

An often-used process control method in chemometrics is the Hotelling $T^2$ chart operating on principal components of the original spectrum/chromatogram. (See, e.g., Russell, E. L.; Chiang, L. H.; Braatz, R. D.; Chemometrics and Intelligent Laboratory Systems, vol. 51, pp. 81–93 (2000); Wilkstrom, C.; Albano, C.; Ericksson, L.; Friden, H.; Johansson, E.; Nordahl, A.; Rannar, S.; Sandberg, M.; Kettaneh-Wold, N.; Wold, S.; Chemometrics and Intelligent Laboratory Systems, vol. 42, pp. 221–231 (1998).) The $T^2$ chart is a multivariate alternative to standard univariate process control methods (see, e.g. Zwillinger, Daniel (ed.), Standard Mathematical Tables and Formulae, 30th Ed. (CRC Press, 1996)), which monitor each variable (e.g., principal component or peak) separately. The $T^2$ chart is a powerful alternative to univariate process control methods because a single test can be used to monitor all variables, and correlation between variables can be accounted for using traditional multivariate techniques.

The $T^2$ test is easy to implement, and requires monitoring of only one statistic. The method can be used to monitor dramatic changes in a monitored process, but it is not adept at identifying gradual or subtle changes over time because it has no memory for recent observations-each observation is compared individually to the training sample. The decision for the current observation is not influenced by the test statistic for preceding observations even if they were almost out of control.

Sequential analysis has been developed to overcome this insensitivity to subtle process changes. Conceptually, a sequential test performs a random sample size hypothesis test:

$H_0$=Spectrum matches reference sample $H_A$=Spectrum does not match reference sample on each spectrum in the sequence until an alternate (out of control) decision is made. Whereas the standard chemometrics methods test a single spectrum at a time for degradation or failure, a sequential test relies on the combined information from current and past observations to make this decision. As a result, sequential tests have been proven to be an improvement in the sense that they are more sensitive (i.e., detect process change more rapidly) than their non-sequential counterparts. (See Ghosh, B. K.; Sen, P. K.; Handbook of Sequential Analysis (Marcel Dekker, Inc., N.Y. 1991) for background on sequential testing.)

In 1954, Page developed a univariate sequential test for the purpose of rapidly detecting a change in processes at random time points. (See Page, E.; Biometrika (1954) pp. 100–114.) Page's test is essentially a modification of Wald's sequential probability ratio test (SPRT) (cf. Wald, A.; Sequential Analysis (Wiley, 1947)) and is known as the cumulative sum ("CUSUM") procedure. Developed for testing the parameters (such as the mean) of univariate random variables, this procedure has many desirable properties. Nonetheless, success of CUSUTM analysis depends on proper selection of its input parameters and accurate modeling of the underlying random variables. There is, therefore, a need for improved modeling of spectral sequences and analysis thereof in relation to the CUSUM procedure.

SUMMARY OF THE INVENTION

One form of the present invention is a unique model for indexed data, applied to determine more accurately whether a sample matches a reference object. Other forms include a unique method for process control based on this unique model wherein a sequence of indexed data sets is analyzed to determine at what point in time the process degrades to an unacceptable state.

In another form of the present invention, one determines whether a sample matches a reference species by selecting N indices $l_j$ of peaks in an indexed data set characterizing the reference species; selecting a first set of probabilities $p_j$ that peaks will occur at the corresponding indices $l_j$, respectively, of an indexed data set that characterizes the sample when the sample matches the reference species; selecting a second set of probabilities $q_j$ that peaks will occur at indices $l_j$, respectively, of an indexed data set that characterizes the sample when the sample does not match the reference species; choosing a threshold $K_c$; obtaining an indexed observation data set $x_1, x_2, \ldots x_N$, where $x_j \in \{0, 1\}$ and $x_j=1$ if and only if a peak is present in the sample at $l_j$; deciding that the sample matches the reference species if $\lambda \leq K_c$ where $$\lambda = \sum_{1 \leq j \leq N} \log\left(\frac{1-p_j}{1-q_j}\right) + \sum_{1 \leq j \leq N} x_j \log\left[\frac{p_j(1-q_j)}{q_j(1-p_j)}\right];$$

and deciding that the sample does not match the reference species if $\lambda > K_c$.

In another form of the present invention, a method is provided for determining whether a sample matches a reference species. From the peaks in an indexed data set, N indices $l_j$ are selected that characterize the reference species. Probabilities $p_i$ and $q_i$ are selected to reflect that peaks will occur in an indexed data set characterizing the sample when the sample does or does not, respectively, match the reference species. A threshold $K_c$ is chosen, and an indexed observation data set $X=x_1, x_2, \ldots x_N$, where $x_j \in \{0, 1\}$ and $x_j=1$ if and only if a peak is present in the sample at index $l_j$. It is decided that the sample matches the reference species if $\lambda \leq K_c$ where $$\lambda = \sum_{1 \leq j \leq N} \log\left(\frac{1-p_j}{1-q_j}\right) + \sum_{1 \leq j \leq N} x_j \log\left[\frac{p_j(1-q_j)}{q_j(1-p_j)}\right];$$

and it is decided that the sample does not match the reference species if $\lambda > K_c$.

In various implementations of this form the invention, one or more of the "selecting" steps is done with iterative proportional scaling, iterative weighed leased squares, or through application of a Lancaster or latent class model.

In another form of the invention, the indices of peaks in an indexed data set characterizing a reference species are selected, and the probabilities that peaks will occur at those indices of an indexed data set that characterizes a sample matching the reference species are selected. A set of probability density functions $g_i(y_i; \theta_i)$ that characterize a measurable feature $y_i$ of the peak at index $l_i$ (given the presence of a peak at index $l_i$) of a data set that characterizes a sample matching the reference species. Probabilities $q_i$ that peaks will occur at indices $l_i$ of an indexed data set that characterizes a non-matching sample, and probability density functions $g_i(y_i; \Omega_i)$ that characterize the measurable feature $y_i$ of the peak at index $l_i$ (given the presence of a peak at index $l_i$) of a data set that characterizes a non-matching sample are selected. A threshold $K_c$ is selected, and an indexed observation data set $x_1, x_2, \ldots x_N$ is obtained (where $x_j \in \{0, 1\}$, and $x_j=1$ if and only if a peak is present in the sample at $l_j$). A feature data set $y_1, y_2, \ldots y_N$ is obtained where $y_i=0$ if no peak is present in the sample at index $l_i$, and where $y_i \in (0, 1\}$ if a peak is present in the sample at index $l_i$. It is decided that the sample matches the reference species if $$\lambda = \sum_{i=1}^{N} \left[\log\frac{1-p_i}{1-q_i} + x_i\left\{\log\frac{p_i(1-q_i)}{q_i(1-p_i)} + \log\frac{g_i(y_i; \theta_i)}{g_i(y_i; \Omega_i)}\right\}\right] \leq K_c,$$

and it is decided that the sample does not match the reference species if $\lambda > K_c$. In various implementations of this invention, $g_i(\cdot)$ is a lognormal, gamma, or Poisson density. In some implementations, the "measurable feature" is the intensity of the peak at index $l_i$, the width of the peak at index $l_i$, or a quantification of the skew of the peak at index $l_i$.

In another form of the invention, the status of a process at any point t in time is characterized by an indexed observation data set $X_t = \{x_{1,t}, x_{2,t}, \ldots x_{N,t}\}$, where $x_{j,t} \in \{0, 1\}$, and $x_{j,t} = 1$ if and only if a peak is present at time t in the sample at index $l_j$. A first set $p_j$ and a second set $q_j$ of probabilities are selected, where $j=1, 2, \ldots N$, and $p_j$ and $q_j$ reflect the probabilities that a peak will occur at index $l_j$ when the process is or is not (respectively) operating normally. A sequence $X_1, X_2, \ldots X_T$ of indexed observation data sets is acquired, and the process is stopped when it is determined that the $C_n$ equals or exceeds a predetermined value A, where $C_0 = 0$;

$C_n = S_n - \min_{1 \leq j \leq n}\{S_j\}$ for $n \geq 1$; and $$S_n = \sum_{1 \leq j \leq N} \log\left(\frac{1-p_j}{1-q_j}\right) + \sum_{1 \leq j \leq N} x_{j,t}\log\left[\frac{p_j(1-q_j)}{q_j(1-p_j)}\right].$$

In one implementation of this form, A is selected as a function of the desired false alarm rate of the test.

In another form of the invention, the status of a process at any point t in time is characterized by an indexed observation data set $X_t = \{x_{1,t}, x_{2,t}, \ldots x_{N,t}\}$, where $x_{j,t} \in \{0, 1\}$, and $x_{j,t} = 1$ if and only if a peak is present at time t in the sample at index $l_j$. A first set $p_j$ and a second set $q_j$ of probabilities are selected, where $j=1, 2, \ldots N$, and $p_j$ and $q_j$ reflect the probabilities that a peak will occur at index $l_j$ when the process is or is not (respectively) operating normally. A first set of probability density functions $g_i(y_i; \theta_i)$ and a second set of probability density functions $g_i(y_i; \Omega_i)$ are selected to characterize a measurable feature $y_i$ of the peak at index $l_i$ (given the presence of such a peak) in a data set that characterizes the sample when the sample matches (or does not match, respectively) the reference species. A sequence $X_1, X_2, \ldots X_T$ of indexed observation data sets is acquired, and the process is stopped when it is determined that the $C_n$ equals or exceeds a predetermined value A, where $C_0 = 0$;

$C_n = S_n - \min_{1 \leq j \leq h}\{S_j\}$ for $n \geq 1$; and $$S_n = \sum_{i=1}^{N} \left[\log\frac{1-p_i}{1-q_i} + x_i\left\{\log\frac{p_i(1-q_i)}{q_i(1-p_i)} + \log\frac{g_i(y_i; \theta_i)}{g_i(y_i; \Omega_i)}\right\}\right].$$

In one implementation of this form, A is selected as a function of the desired false alarm rate of the test. In some implementations, at least one of the probability density functions $g_i(\cdot)$ is either a normal, lognormal, gamma, or Poisson density function.

Still another form of the present invention is a system for analyzing a sample in comparison with a reference species, comprising a processor, a memory, and a computer-readable medium. The memory stores data indicative of probabilities $p_j$ ($j=1, 2, \ldots N$) that peaks will occur at indices $l_j$ of an indexed data set that characterizes a sample matching the reference species; data indicative of probabilities $q_j$ that peaks will occur at indices $l_j$ of an indexed data set that characterizes a sample not matching the reference species; data indicative of a threshold value; and an indexed sample data set $x_j$ characterizing the sample, wherein each $x_j$ is a binary value that indicates whether or not a peak is present at index $l_j$. The computer-readable medium is encoded with programming instructions executable by the processor to calculate a log-likelihood ratio $$\lambda = \sum_{1 \leq j \leq N} \log\left(\frac{1-p_j}{1-q_j}\right) + \sum_{1 \leq j \leq N} x_j\log\left[\frac{p_j(1-q_j)}{q_j(1-p_j)}\right],$$

to generate a first signal when $\lambda$ is less than the threshold value, and to generate a second signal when $\lambda$ is greater than the threshold value.

In some embodiments of this form, $K_c$ is selected such that, given that the sample matches the reference species, $P\{\lambda > K_c\} \leq \alpha$ for a predetermined type I error probability $\alpha$. In other embodiments, the selecting steps comprise iterative proportional scaling calculations, iterative weighted least squares calculations, or application of a Lancaster model or latent class model.

Yet another form of the present invention is a method of determining whether a sample matches a reference species. The method includes selecting N indices $l_j$ of peaks in an indexed data set characterizing the reference species; selecting a first set of probabilities $p_j$ that peaks will occur at indices $l_j$, respectively, of an indexed data set that characterizes the sample when the sample matches the reference species; selecting a first set of probability density functions $g_i(y_i; \theta_i)$ that characterize a measurable feature $y_i$ of the peak at index $l_i$ given the presence of a peak at index $l_i$ in a data set that characterizes the sample when the sample matches the reference species; selecting a second set of probabilities $q_j$ that peaks will occur at indices $l_j$ of an indexed data set that characterizes the sample when the sample does not match the reference species; selecting a second set of probability density functions $g_i(y_i; \Omega_i)$ that characterize the measurable feature $y_i$ of the peak at index $l_i$ given the presence of such a peak in a data set that characterizes the sample when the sample does not match the reference species; selecting a threshold $K_c$; obtaining an indexed observation data set $x_1, x_2, \ldots x_N$ where $x_i \in \{0, 1\}$ and $x_i = 1$ if and only if a peak is present in the sample at $l_i$; deciding (a) that the sample matches the reference species if $\lambda \leq K_c$ where $$\lambda = \sum_{i=1}^{N} \left[ \log \frac{1-p_i}{1-q_i} + x_i \left\{ \log \frac{p_i(1-q_i)}{q_i(1-p_i)} + \log \frac{g_i(y_i; \theta_i)}{g_i(y_i; \Omega_i)} \right\} \right]$$

or (b) that the sample does not match the reference species if $\lambda > K_c$.

In some embodiments of this form, one or more $g_i(\cdot)$ are lognormal densities given by $$g_i(y_i; \theta_i) = q_i(y_i; \mu_i, \sigma_i^2) = \frac{1}{y_i \sqrt{2\pi\sigma_i^2}} \exp\left\{ -\frac{(\log y_i - \mu_i)^2}{2\sigma_i^2} \right\}, y_i \geq 0.$$

In some other embodiments, one or more $g_i(\cdot)$ are gamma densities given by $$g_i(y_i; \theta_i) = q_i(y_i; \alpha_i, \beta_i) = \frac{1}{\Gamma_{\alpha_i} \beta_i^{\alpha_i}} y_i^{\alpha_i - 1} \exp(-y_i / \beta_i), y_i \geq 0.$$

In still other embodiments, one or more $g_i(\cdot)$ are Poisson densities given by $$g_i(y_i; \theta_i) = \frac{\theta^{y_i} \exp(-\theta_i)}{y_i!}, y_i = 0, 1, 2, \ldots.$$

In some embodiments of this form of the invention, the measurable feature is the intensity of the peak at index $l_i$. In other embodiments, the measurable feature is the width of the peak at index $l_i$; while in still other embodiments, the measurable feature is a quantification of the skew of the peak at index $l_i$.

In yet another form of the invention, various distinct classes of spectra are created, each with $p_i$ and $q_i$ (and possibly $g_i(y_i; \theta_i)$ and $g_i(y_i; \Omega_i)$) derived from control spectra. The spectrum for a sample is obtained, and a $\lambda$ is calculated for the spectrum relative to the model for each class. The sample is associated with one of the distinct classes using a maximum likelihood approach, i.e., the class for which the $\lambda$ obtained.

Still another form of the invention is in the field of cluster analysis, wherein the analysis described herein is applied to identify distinct classes or groups in a set of spectra. In doing so, one may embed the comparison technique disclosed herein in cluster analysis techniques such as k-means, hierarchical, leader, and fuzzy clustering methods.

A further form of the invention is in hypothesis testing, with applications in process control (as discussed in detail herein), simple or composite hypothesis testing, analysis of variance, or other statistical procedures involving multiple comparisons.

Still further forms of the invention will occur to one skilled in the art in light of the disclosure herein.

BRIEF DESCRIPTION OF THE DRAWINGS

FIG. 4 is a table of actual significance levels for a hypothesis test according to one form of the invention.

FIGS. 8a–8c are graphs of the raw spectrum, weighted variance values, and peak table, respectively for a reference species.

DETAILED DESCRIPTION

Figure 1:
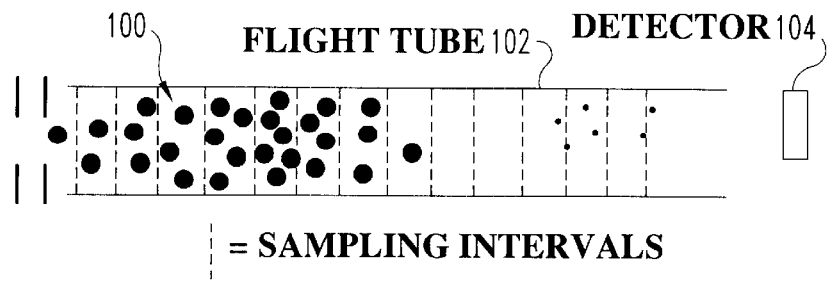
FIG. 1 is exemplary of time-of-flight mass spectrometry according to the prior art, depicting particles of different masses being separated while traveling through a flight tube, the particles having different velocities, such that particles of a given mass and charge are binned as according to the sampling interval of the detector.
Figure 2:
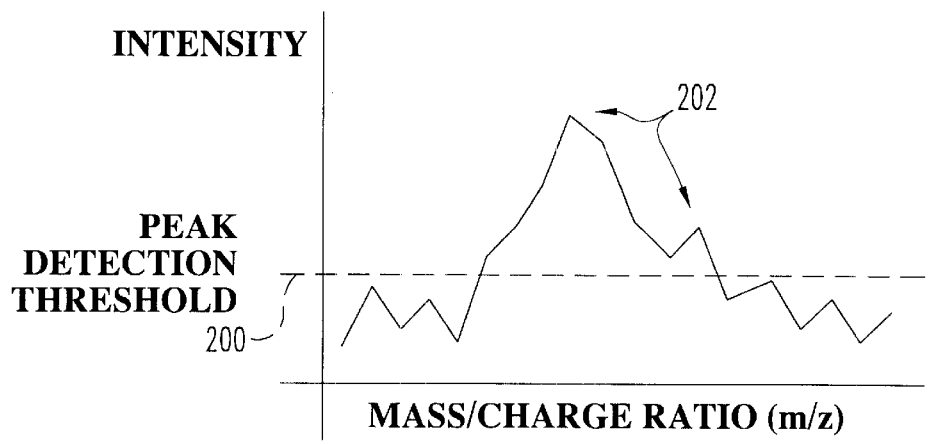
FIG. 2 is exemplary of a MALDI-MS spectrum using a prior art method of determining a peak detection threshold.
Figure 3:
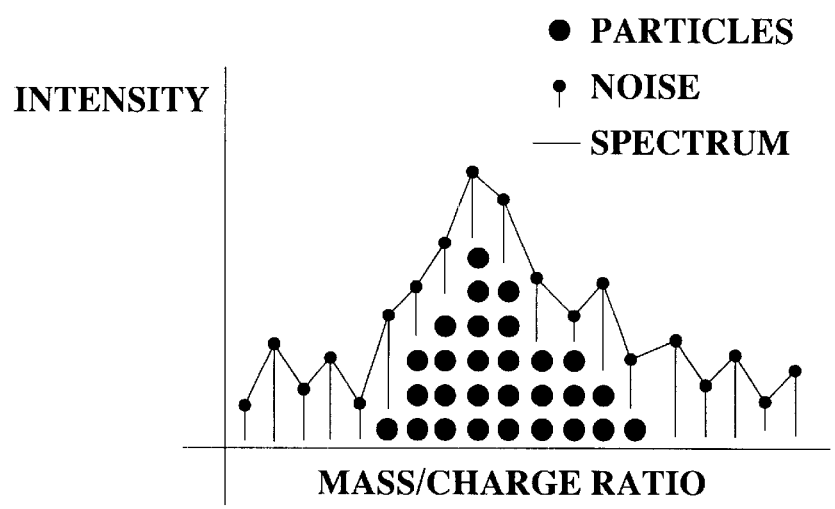
FIG. 3 illustrates the concept of a spectrum as a histogram, or sequence of bins containing and measuring particle counts augmented by measurement uncertainty, for use in relation with the present invention.

For the purpose of promoting an understanding of the principles of the invention, reference will now be made to the embodiments illustrated in the drawings, and specific language will be used to describe the same. It will, nevertheless, be understood that no limitation of the scope of the invention is thereby intended. Any alterations and further modifications in the described embodiments and any further application of the principles of the invention as described herein are contemplated as would normally occur to one skilled in the art to which the invention relates.

The present invention encompasses methods of applying characterizations of reference indexed data to sample testing and process control, as well as equipment configured to perform such methods. Such indexed data may be provided as spectral data obtained from processes including but not limited to mass spectrometry (MS); gas chromatography (GC); and nuclear magnetic resonance (NMR), Auger, infrared and RAMAN spectroscopy. The present invention also encompasses other forms of indexed data analysis, including but not limited to numerical transforms of data such as Fourier, fast Fourier, and wavelet transforms; time series data such as financial stock or bond market time series; acoustic transducer or other sensor output; and automobile traffic monitoring or other counting processes.

Where the term "index" is used herein, it will be understood to encompass one or more parameters including but not limited to time, distance, frequency, location, an identifier parameter (for example, demographic data), index number and combinations thereof. The term "indexed data" is understood to include, but is not limited to, sets of ordered data which can be expressed as ordered pairs (index, response), or as ordered multiples (index1, index2, . . . response) from multi-dimensional analyses. Such data may be derived from analyses including, but not limited to, two dimensional (2-D) mass spectrometry (MS—MS), 2-D gas chromatography (GC—GC), 2-D liquid chromatography and mass spectrometry (LC—LC-MS), 2-D Fourier transforms, 2-D bio-chip micro-arrays, 2-D electrophoresis gels, 3-D nuclear magnetic resonance microscopy, and combinations thereof.

Figure 11:
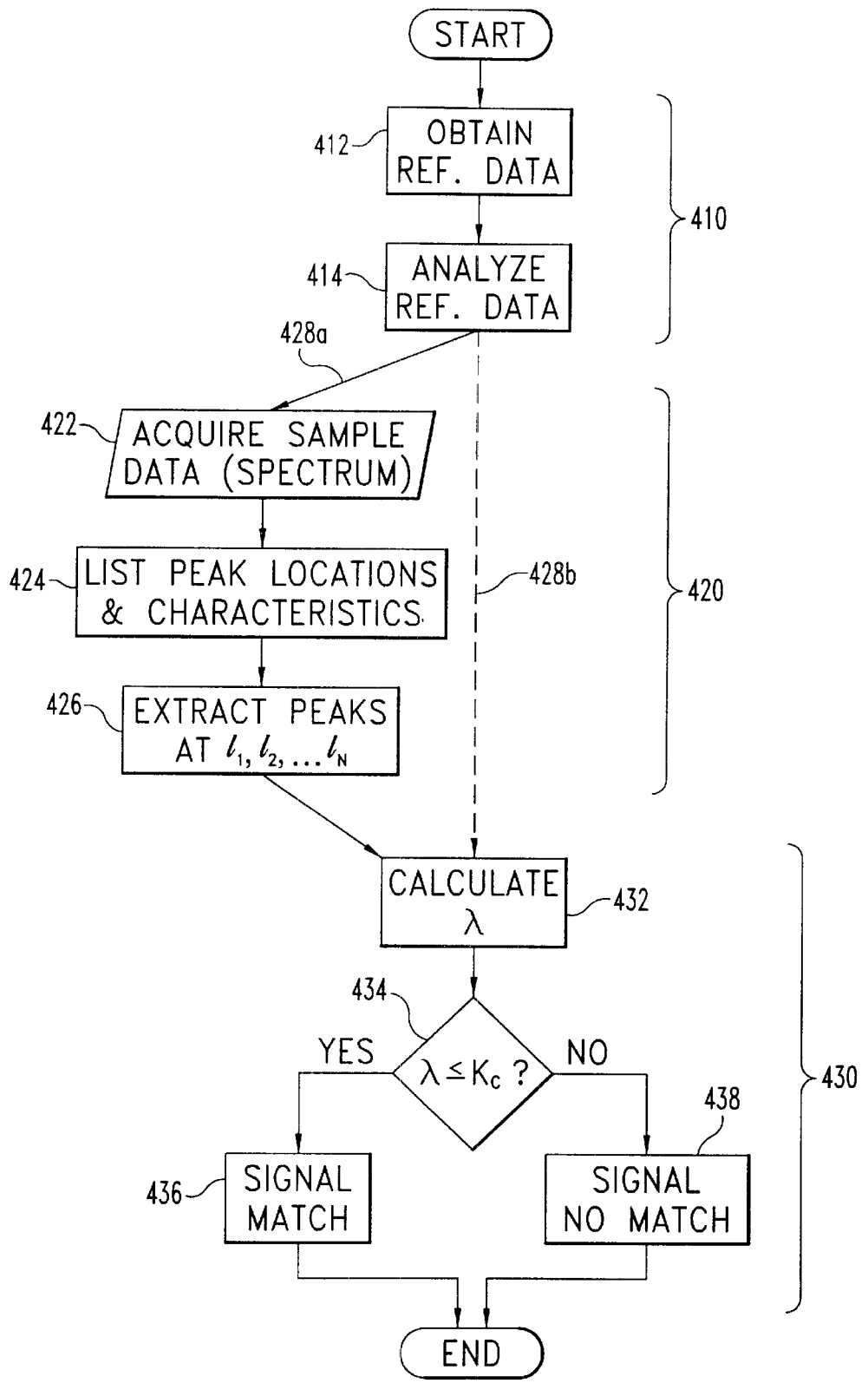
FIG. 11 is a flow chart of a method for determining whether a sample matches a reference species according to the present invention.

The analytical process 400 described herein proceeds generally as illustrated in FIG. 11. First, reference data is characterized at 410. Indexed data sets $X_1, X_2, \ldots X_N$ are obtained 412 for one or more reference objects. These data sets are analyzed 414 to determine the locations (indices) $l_1, l_2, \ldots l_N$ of N peaks that characterize the reference data. For each $l_i$, $x_i \in \{0, 1\}$; $x_i = 1$ if and only if a peak is present in the indexed data set at location $l_i$. Given these data sets for the reference objects, known methods may be used to obtain probabilities $p_i$: i=1, 2, . . . N that the peak will appear at index $l_i$ given the null hypothesis $H_0$. Similar methods may be used to determine probabilities $q_i$: i=1, 2, . . . N that the feature will exist at index $l_i$ given the alternative hypothesis $H_A$.

Data relating to the sample to be tested is then examined 420. An indexed data set is acquired 422 for the sample, and the peak locations and characteristics in that spectrum are listed 424. The peaks at $l_1, l_2, \ldots l_N$ are extracted 426 for later processing.

In some embodiments, it will be convenient for the processing 410 of the reference material to be done before the processing 420 of the test sample. This sequence is shown along path 428a. In other embodiments, the processing 410 of the reference material may be done in parallel with the processing 420 of the sample, as shown with path 428b. Those skilled in the art will appreciate that these and other tasks discussed herein may be performed in series or in parallel as desired or useful in various situations.

When the peak data has been collected for the reference species and the test sample, $\lambda$ is calculated according to equation (10) as discussed below. If the calculated value $\lambda$ is less than or equal to a predetermined threshold $K_c$ (positive result at decision block 434), the test sample is determined to have matched the reference species, and that match is signaled accordingly at 436. If $\lambda > K_c$ (negative result at decision block 434), the test sample is deemed to not match the reference species, and the mismatch is signaled at bock 438.

Figure 12:
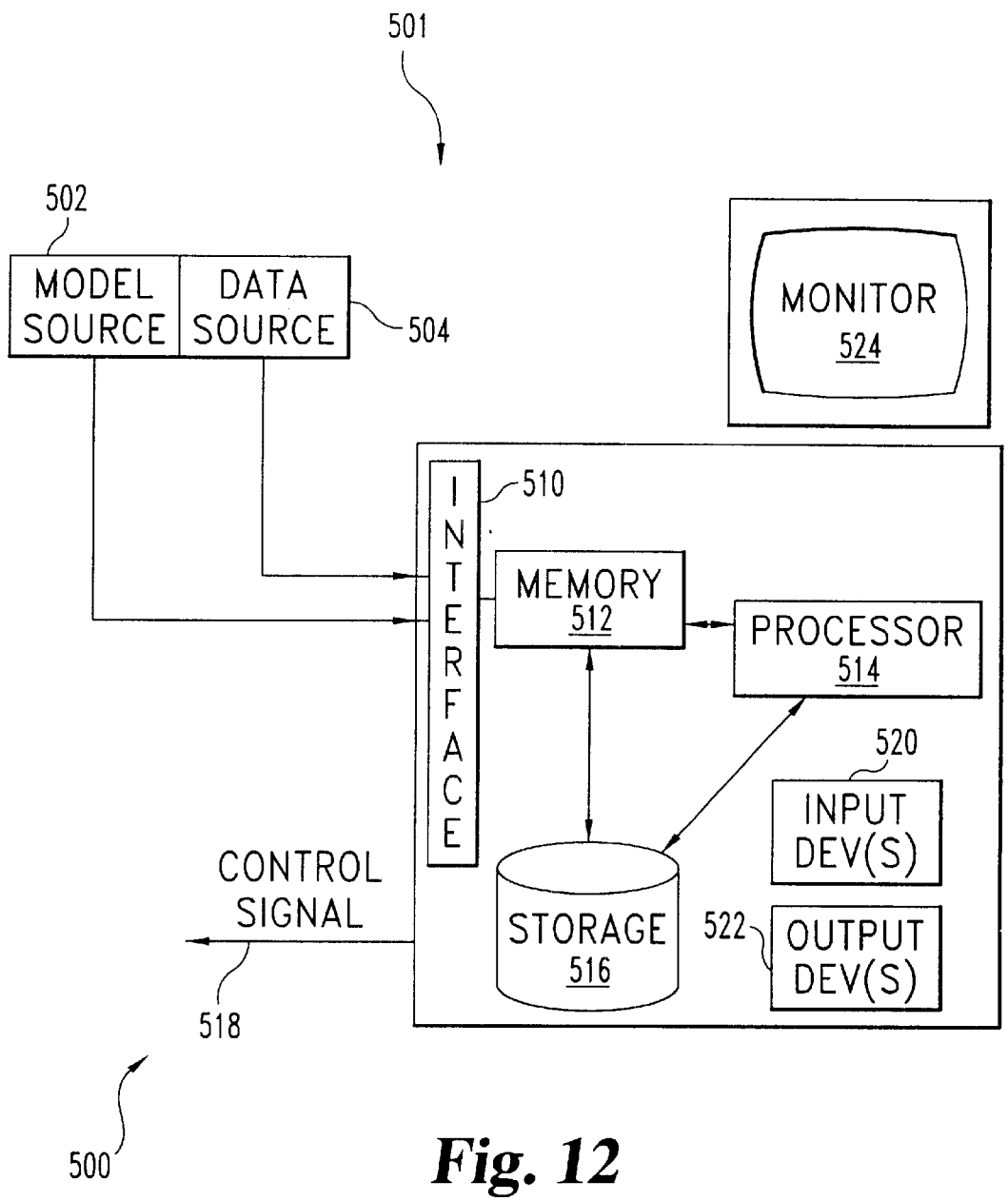
FIG. 12 is a block diagram of a system for performing computations in conjunction with the present invention.

A system 500 that implements one embodiment of the present invention will now be discussed in relation to FIG. 12. In this exemplary embodiment, the various hardware and software components that implement the steps and features discussed herein are combined in workstation 501. The software programs and modules described herein are encoded on storage device 516 for execution by processor 514. Workstation 501 may include more than one processor or CPU and more than one type of memory 512, where memory 512 is representative of one or more types. Furthermore, it should be understood that while one workstation 501 is illustrated, more workstations may be utilized in alternative embodiments. Processor 514 may be comprised of one or more components configured as a single unit. Alternatively, when of a multi-component form, processor 514 may have one or more components located remotely relative to the others. One or more components of processor 514 may be of the electronic variety defining digital circuitry, analog circuitry, or both. In one embodiment, processor 514 is of a conventional, integrated circuit microprocessor arrangement, such as one or more PENTIUM III or PENTIUM 4 processors supplied by INTEL Corporation of 2200 Mission College Boulevard, Santa Clara, Calif., 95052, USA.

Memory 512 may include one or more types of solid-state electronic memory, magnetic memory, or optical memory, just to name a few. By way of non-limiting example, memory 246 may include solid-state electronic Random Access Memory (RAM), Sequentially Accessible Memory (SAM) (such as the First-In, First-Out (FIFO) variety or the Last-In First-Out (LIFO) variety), Programmable Read Only Memory (PROM), Electrically Programmable Read Only Memory (EPROM), or Electrically Erasable Programmable Read Only Memory (EEPROM); an optical disc memory (such as a DVD or CD ROM); a magnetically encoded hard disc, floppy disc, tape, or cartridge media; or a combination of any of these memory types. Also, memory 512 may be volatile, nonvolatile, or a hybrid combination of volatile and nonvolatile varieties. Storage device 516 may take any one or more of these forms as well, independently from the form(s) of memory 512.

Monitor 524 provides visual output from workstation 501 to live operators. Optional additional input device(s) 520 and optional output device(s) 522 provide interfaces with other computing and/or human entities. Further, workstation 501 may include additional and/or alternative components as would occur to one skilled in the art.

Furthermore, in various embodiments of the invention, the data sent to workstation 501 by model data source 502 and sample data source 504 may be stored and processed in digital and/or analog form. Interface 510 may be any suitable device, including, for example, a parallel port, serial port, or network interface card, as desired or needed in a particular implementation.

A more realistic model allows for correlation between the appearance of peaks. In such a model, for example, the probability of the appearance of a mass spectral peak at 4500 Daltons would be higher if a peak is observed at 9000 Daltons than if no peak is observed at 9000 Daltons, due to the potential for doubly charged ions. Intuitively, this model results in a series of conditional probabilities for peak appearance dependent on other ions observed. For example, consider only the possibility of singly and doubly charged ions. Let $p_m$ represent the probability of appearance of a singly charged fingerprint peak at m/z=m, and $x_m = 0$ if the ion is not observed and $x_m = 1$ if it is observed. Then the probability of appearance of a peak at m/2 can be described in terms of a conditional probability dependent on whether $x_m = 0$ or $x_m = 1$. In particular, we define $$p_{m/2|x_m} = P\{x_{m/2}=1|x_m\}. \tag{1}$$

The likelihood of outcomes for these two peaks then becomes $$P\{x_m = i, x_{m/2} = j\} = \begin{cases} (1-p_m)(1-p_{m/2|x_m=0}) & i=j=0 \\ (1-p_m)p_{m/2|x_m=0} & i=0, j=1 \\ p_m(1-p_{m/2|x_m=1}) & i=1, j=0 \\ p_m p_{m/2|x_m=1} & i=j=1 \end{cases} \tag{2}$$

We note that the probability of appearance of a triply charged ion can be computed in the same manner by conditioning on both $x_m$ and $x_{m/2}$, and the resulting likelihood function would contain $2^3=8$ possible outcomes.

Specifying all possible dependencies in this manner is impractical. For example, if a typical spectrum contains twenty peaks, then accounting for all possible pairwise dependencies between peaks yields $2^{20}-1$ conditional probability values that need to be computed for each peak. But if we restrict attention to second-order dependencies (i.e., peak pairs and triples), we can obtain a more parsimonious (and hence more computable) model for the dependencies. The dependencies can be computed using a reduced-order loglinear model. A second-order loglinear model, which accounts for all dependencies between pairs of peaks, is given by $$\log h(x) = \theta' u(x), \tag{3}$$

where $$u(x) = \begin{pmatrix} 1 \\ x_1 \\ \vdots \\ x_N \\ x_1 x_2 \\ \vdots \\ x_{N-1} x_N \end{pmatrix} \tag{4}$$

and $\theta$ is a vector of $$N + \binom{N}{2}$$

parameters to be estimated. For N=20, 211 parameters must be estimated to account for all dependent pairs. These parameters can be estimated using standard statistical estimation techniques, such as iterative proportional scaling or iterative weighted least squares. Other convenient models, such as Lancaster models and latent class models, can be used to model correlations among binary variables.

Teugels (Teugels, J. L., Journal of Multivariate Analysis, vol. 32, pp. 256–268 (1990)) provides another alternative to the loglinear approach for modeling dependencies. In this work, the author proves that the multivariate Bernoulli distribution can be described through a set of $2^{N-1}$ parameters, where N is the number of variates (peaks) in the distribution. Specifically, the probability distribution for the presence of peaks can be described by the set $p_i$; i=1, 2, . . . N and the following dependency parameters:

$$\sigma_x^{(n)} = E\left[\prod_{1 \le i \le N} (X_i - p_i)^{x_i}\right]; x_i = 0, 1 \tag{5}$$

Equation (5) contains $2^N$ parameters. We note that one of these parameters can be eliminated because of the requirement that the probabilities of all possible combinations must sum to one. We also note that when x=1 for some i and 0 for all j≠i, then the dependency parameter $\sigma_x^{(n)}$ is zero. To fully characterize all pairwise dependencies, we include in equation (5) only cases where two of the $x_i$ are 1, and all others are zero. In this case, $$N + \binom{N}{2}$$

parameters are required to completely specify the distribution.

This approach works directly from the exact distribution for peak presence rather than using the traditional loglinear approximations. By eliminating the loglinear approximation, it is possible that more accurate data analysis methods can be developed.

The present method relies on a reference fingerprint that characterizes the statistical properties of a spectrum under nominal conditions (i.e., a null hypothesis). The comparison is performed as a hypothesis test for the following:

$H_0$: spectrum matches the reference fingerprint $H_A$: spectrum does not match the reference fingerprint (6)

To test for the presence of fingerprint peaks at indices $l_i$: i=1, 2, . . . N, the comparison procedure is a likelihood ratio test for $H_0$ versus $H_A$ and proceeds in three general steps. In the first step, a peak table is constructed from the test spectrum that contains a list of the peak locations and characteristics of any peaks in the test sample. In the second step, any reference fingerprint peaks appearing in the peak table of the test sample are extracted using a prediction interval based on the t-distribution.

The hypothesis test described by equation (6) is performed in the third step of the process. In particular, under the null hypothesis $H_0$, the frequency of appearance of a peak at fingerprint peak location $l_i$ is given by some probability $q_i$. Under the alternative hypothesis $H_A$, where the spectrum does not match the reference, the frequency of appearance of a peak at fingerprint peak location $l_i$ is given by the probability $p_i$ reflecting the occurrence of spurious, false, or background peaks.

Let $x_i=0$ if fingerprint peak i is not observed in the unknown sample, and $x_i=1$ if fingerprint peak i is observed in the unknown sample. Ignoring dependencies between presence of different peaks, then the likelihood ratio for the hypothesis test given in equation (6) is given by $$L = \frac{P\{\text{outcome under } H_A\}}{P\{\text{outcome under } H_0\}} \tag{7}$$

$$= \frac{\prod_{1 \le j \le N} p_j^{x_j} \prod_{1 \le j \le N} (1-p_j)^{1-x_j}}{\prod_{1 \le j \le N} q_j^{x_j} \prod_{1 \le j \le N} (1-q_j)^{1-x_j}}$$

where N is the number of reference peaks in F. In practice, the log-likelihood ratio $\lambda = \log(L)$ is used where $$\lambda = \sum_{1 \le j \le N} \log\left(\frac{1-p_j}{1-q_j}\right) + \sum_{1 \le j \le N} x_j \log\left[\frac{p_j(1-q_j)}{q_j(1-p_j)}\right] \quad (8)$$

In performing the test, the following decision rule is applied:

If $\lambda \le K_c$, then accept $H_0$,

If $\lambda > K_c$, then reject $H_0$.

If $H_0$ is rejected, the reference species is determined to be present in the unknown sample.

The critical threshold $K_c$ is determined by the desired significance level of the test as follows. The probability of falsely rejecting the null hypothesis is given by $$\alpha = P\{\lambda > K_C | H_0\} \quad (9)$$

$$= P\left\{\sum_{1 \le j \le N} \log\left(\frac{1-p_j}{1-q_j}\right) + \sum_{1 \le j \le N} x_j \log\left[\frac{p_j(1-q_j)}{q_j(1-p_j)}\right] > K_C | H_0\right\}$$

The threshold $K_c$ is set by fixing a desired false alarm (type I error) probability $\alpha$ and finding the smallest value of $K_c$ that yields $$P\{\lambda > K_c | H_0\} \le \alpha. \quad (10)$$

When the number of fingerprint peaks N is small, $K_c$ can easily be obtained by enumerating and computing the probability of all possible combinations of outcomes $\{x_j; j=1, 2, \ldots N\}$ under the null hypothesis, and finding the $K_c$ that meets equation (10). When the number of fingerprint peaks N is large, however, enumerating all $2^N$ possible outcomes becomes computationally difficult. Therefore, when $N \ge 10$, we approximate the statistical distribution of the log-likelihood ratio $\lambda$ with a normal approximation, where $$E[\lambda] = \sum_{1 \le j \le N} \log\left(\frac{1-p_j}{1-q_j}\right) + \sum_{1 \le j \le N} q_j \log\left[\frac{p_j(1-q_j)}{q_j(1-p_j)}\right] \quad (11)$$

$$Var[\lambda] = \sum_{1 \le j \le N} q_j(1-q_j)\left\{\log\left[\frac{p_j(1-q_j)}{q_j(1-p_j)}\right]\right\}^2$$

under the null hypothesis. We note that under the alternative hypothesis, the $q_j$ and $(1-q_j)$ immediately following the second summation in $E[\lambda]$ and $Var[\lambda]$ are replaced by $p_j$ and $(1-p_j)$, respectively. By modifying equation (11) in this way, expressions for the type II error and power of the test can be estimated when N is large.

The question of how accurately the normal distribution approximates that of $\lambda$ arises. FIG. 4 gives the actual significance level of the test when the normal approximation is used for various values of $p_j$, $q_j$, and N. The actual significance level is computed from the exact distribution obtained by enumerating all possible outcomes. From FIG. 4, one can see that the approximation tends to be conservative in the sense that the actual significance level of the test is smaller than the specified level, except when $\alpha$ is small. In the cases of $\alpha=0.01$ and $\alpha=0.001$, the actual type I error tends to be larger than the specified level when the $p_j$ are split between 0.7 and 0.9. Overall, the results of FIG. 4 suggest that the normal approximation is sufficient for $N \ge 8$, however, when a small significance level is desired, the specified value of $\alpha$ should probably be set smaller than the desired significance level to ensure that the performance of the test is adequate.

The two-stage model builds on the one-stage model by combining the discrete (binary) peak presence distribution with continuous peak characteristic (e.g., intensity, skew, or width) information. For example, peak intensity may be characterized given that a peak is present. Let $y_i$ denote the peak intensity at location $l_i$. Clearly $y_i=0$ if $x_i=0$; if $x_i=1$, then $y_i$ assumes a positive, continuous-valued distribution $g_i(y_i;\theta_i)$. It is convenient to take $g_i$ to be the normal distribution, with density $$g_i(y_i; \mu_i, \sigma_i^2) = \frac{1}{\sqrt{2\pi\sigma_i^2}} \exp\left\{-\frac{(y_i - \mu_i)^2}{2\sigma_i^2}\right\}, \quad (12)$$

but the normal distribution is not positive-valued (i.e., variables can take values less than zero), so it is preferred to use distributions such as the lognormal and the gamma, which are defined for non-negative real numbers, or the Poisson distribution, which is defined for non-negative integers. The lognormal density is given by $$g_i(y_i; \mu_i, \sigma_i^2) = \frac{1}{y_i\sqrt{2\pi\sigma^2}} \exp\left\{-\frac{(\log y_i - \mu_i)^2}{2\sigma_i^2}\right\}, \quad y_i \ge 0, \quad (13)$$

the gamma density is given by $$g_i(y_i; \alpha_i, \beta_i) = \frac{1}{\Gamma_{\alpha_i}\beta_i^{\alpha_i}} y_i^{\alpha_i - 1} \exp(-y_i/\beta_i), \quad y_i \ge 0, \quad (14)$$

and the Poisson density is given by $$g_i(y_i, \theta_i) = \frac{\theta^{y_i}\exp(-\theta_i)}{y_i!}, \quad y_i = 0, 1, 2, \ldots \quad (15)$$

The joint distribution of $x_i$ and $y_i$ is $$f(x_i,y_i) = h_i(x_i)g_i(y_i|x_i) = p_i^{x_i}(1-p_i)^{1-x_i}(1_{(y_i=0)})^{1-x_i}g_i(y_i;\theta_i)^{x_i}, \quad (15.1)$$

where $g_i$ is one of the densities (13)–(15). For the two stage model given in equation (15.1), the log-likelihood ratio is then $$\lambda = \sum_{i=1}^{N}\left[\log\frac{1-p_i}{1-q_i} + x_i\left\{\log\frac{p_i(1-q_i)}{q_i(1-p_i)} + \log\frac{g_i(y_i; \theta_i)}{g_i(y_i; \Omega_i)}\right\}\right], \quad (16)$$

where $\{q_i, \Omega_i\}$ and $\{p_i, \theta_i\}$ are the model parameters under the null hypothesis (of reference peaks) and alternative hypothesis (of background peaks), respectively. The expectation and variance of $\lambda$ depend on the choice of $g_i(y_i; \theta_i)$. We compute the expectation and variance under the Poisson, normal, lognormal and gamma distributions.

Poisson model

If the conditional intensity random variables conform to the Poisson density (in equation (15)) with parameter $\Omega_i$ under the null hypothesis $H_0$ (that the spectrum matches reference fingerprint), and with parameter $\theta_i$ under the alternative hypothesis $H_A$ (that the spectrum does not match the reference fingerprint), then $$E[\lambda] = \sum_{1 \le j \le N}\left[\log\frac{1-p_j}{1-q_j} + \quad (17)\right.$$

-continued $$q_j\left(\log\frac{p_j(1-q_j)}{q_j(1-p_j)} + \Omega_j - \theta_j + \Omega_j\log\frac{\theta_j}{\Omega_j}\right)\bigg],$$

and $$Var[\lambda] = \sum_{1\le j\le N}\left[q_j\Omega_j\left(\log\frac{\theta_j}{\Omega_j}\right)^2 + \left(\log\frac{p_j(1-q_j)}{q_j(1-p_j)} + \Omega_j - \theta_j + \Omega_j\log\frac{\theta_j}{\Omega_j}\right)^2 q_j(1-q_j)\right]. \quad (18)$$

Normal model

If the conditional intensity random variables conform to the normal density (12) with parameters $\Omega_j=(\nu_j,\tau_j^2)$ under $H_0$ and $\theta_j=(\mu_j,\sigma_j^2)$ under $H_A$, then $$E[\lambda] = \sum_{1\le j\le N}\left[\log\frac{1-p_j}{1-q_j} + q_j\left(\log\frac{p_j(1-q_j)}{q_j(1-p_j)} + \frac{1}{2}\log\frac{\tau_j^2}{\sigma_j^2} - \frac{1}{2\sigma_j^2}[\tau_j^2 + (\nu_j-\mu_j)^2] + \frac{1}{2}\right)\right] \quad (19)$$

and $$Var[\lambda] = \sum_{1\le j\le N}\left[q_j(1-q_j)\left[a + \frac{\sigma_j^2-\tau_j^2}{2\sigma_j^2}\right]^2 + q_j\left[\left(\frac{\sigma_j^2-\tau_j^2}{2\sigma_j^2}\right) + \left(\frac{\tau_j}{\sigma_j^2}(\nu_j-\mu_j)\right)^2\right]\right] \quad (19)$$

where $$a = \log\frac{p_j(1-q_j)}{q_j(1-p_j)} + \frac{1}{2}\log\frac{\tau_j^2}{\sigma_j^2} - \frac{(\nu_j-\mu_j)^2}{2\sigma_j^2}.$$

Lognormal model

If the conditional intensity random variables conform to the lognormal model (13) with parameters $\Omega_j=(\nu_j,\tau_j^2)$ and $\theta_j=(\mu_j,\sigma_j^2)$, then $E(\lambda)$ and $Var(\lambda)$ are identical to those obtained under the normal model (see equations (21) and (22)).

Gamma model

If the conditional intensities conform to the gamma model (16) with parameters $\Omega_j=(\rho_j,\gamma_j)$ under $H_0$ and $\theta_j=(\alpha_j,\beta_j)$ under $H_A$, then $$E[\lambda] = \sum_{1\le j\le N}\left[\log\frac{1-p_j}{1-q_j} + q_j\left(\log\frac{p_j(1-q_j)\gamma_j^{\rho_j}\Gamma_{\rho_j}}{q_j(1-p_j)\beta_j^{\alpha_j}\Gamma_{\alpha_j}} + p_j\left(\frac{\beta_j-\gamma_j}{\beta_j}\right) + (\alpha_j-\rho_j)\Psi_j(\rho_j,\gamma_j)\right)\right]$$

and $$Var(\lambda) = \sum_{1\le j\le N}[q_j(1-q_j)K^2 + q_j(L_j^2\rho_j + (\alpha_j-\rho_j)^2\Theta_j(\rho_j,\gamma)\rho_j + 2(\alpha_j-\rho)L_j\rho_j\Psi_j(\rho_j,\gamma_j))]$$

where $$K = \log\frac{p_j(1-q_j)\gamma_j^{\rho_j}\Gamma_{\rho_j}}{q_j(1-p_j)\beta_j^{\alpha_j}\Gamma_{\alpha_j}} + \rho_j\frac{\beta_j-\gamma_j}{\beta_j} + (\alpha_j-\rho_j)\Psi_j(\rho_j,\gamma_j),$$

$$\Psi_j(\rho_J,\gamma_J)=E(\log Y_j;\rho_J,\gamma_J),$$

and $$\Theta_j(\rho_J,\gamma_J)=Var(\log Y_j;\rho_J,\gamma_J).$$

Process Control

We now discuss a multivariate CUSUM procedure for control of analytical processes based on the model presented above. Let $X_1, X_2, \ldots$ be a sequence of spectra where $X_1, X_2, \ldots X_{k-1}$ follow $H_0$ and $X_k, X_{k+1}, \ldots$ follow $H_A$. In other words, the process follows some prescribed nominal behavior until time k>1, called the "change point," at which time the process behavior changes. The CUSUM approach considers the sequence $Z_i=g(X_i)-c$, where c is a constant, and $g(\cdot)$ is a function of an incoming spectrum. We let $S_n=\Sigma_{1\le j\le n}Z_j$, and define the test statistic to be $C_n=S_n-\min_{1\le j\le n}\{S_j\}$ for $n\ge 1$ with $C_0=0$. Then $C_n$ can be formulated recursively by the relation $C_{n+1}=\max\{0, C_n+Z_{n+1}\}$. This process is repeated for incoming observations until $C_n\ge A$ for some constant A, at which time the process is declared to be out of control. The constant A is determined by the desired false alarm frequency of the test. In the traditional univariate setting, A can be specified according to the method presented in Khan, R.; *Journal of Statistical Planning and Inference*, vol. 2, pp. 63–77 (1978). Specification of A for the test developed here will be discussed in further detail in the following section.

To determine the increments $Z_i$; $i=1, 2, \ldots$, we construct the likelihood ratio about the change point k. To this end, we represent the probability density of the observations up to time n given change point k by $$f_{k,n}(x_1,x_2,\ldots x_n) = \prod_{j=1}^{k-1} f_0(x_j)\prod_{l=k}^{n} f_1(x_l) \quad (20)$$

Based on the likelihood ratio for a particular change point, we then define the following stopping rule:

$$R = \min\left\{n: n\ge 1, \lambda_{k,n} = \frac{f_{k,n}(x_1, x_2, \ldots x_n)}{f_0(x_1)f_0(x_2)\ldots f_0(x_n)} \ge A_k,\right.$$
$$\left. \text{for any } k = 1, 2, \ldots n\right\} \quad (21)$$

where $A_k$ is a sequence of positive constants which relate to the decision threshold given a change point $k=1, 2 \ldots$ The random variable R is called the run length of the test and indicates the first time the process is determined to be out of control. In practice, this modified CUSUM procedure is implemented by taking the logarithm of the likelihood ratio $\lambda_{k,n}$. Letting $Z_i=\lambda_{k,n}$ derived from equation (8), it can be shown (see Ghosh, supra) that this stopping rule is equivalent to $$R=\min\{n:C_n\ge A\} \quad (22)$$

In the case of the model presented here, we derive a CUSUM procedure by letting $Z_n$ be given by the likelihood ratios (8) or (16) and applying the stopping rule given in (22).

Figure 5A:
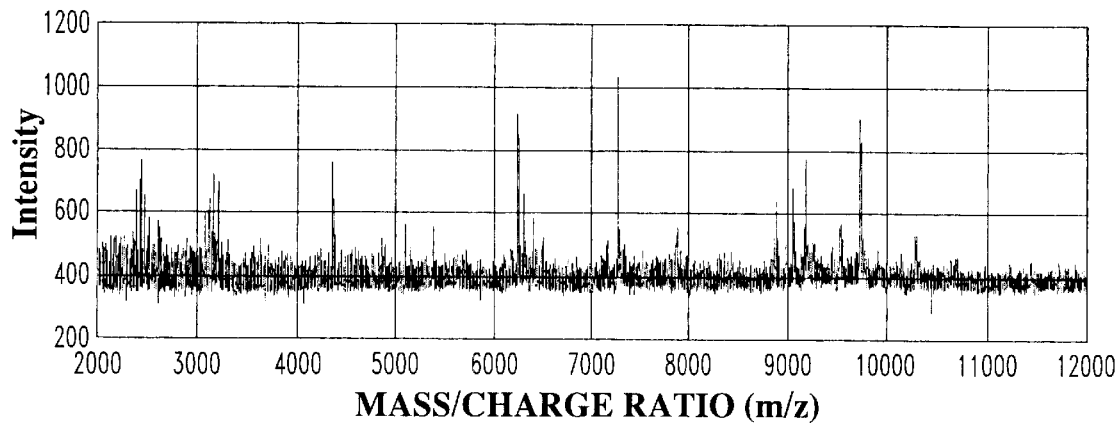
FIG. 5a is a MALDI-MS spectrum graph for a pure *E. coli* culture, as is known in the art.
Figure 5B:
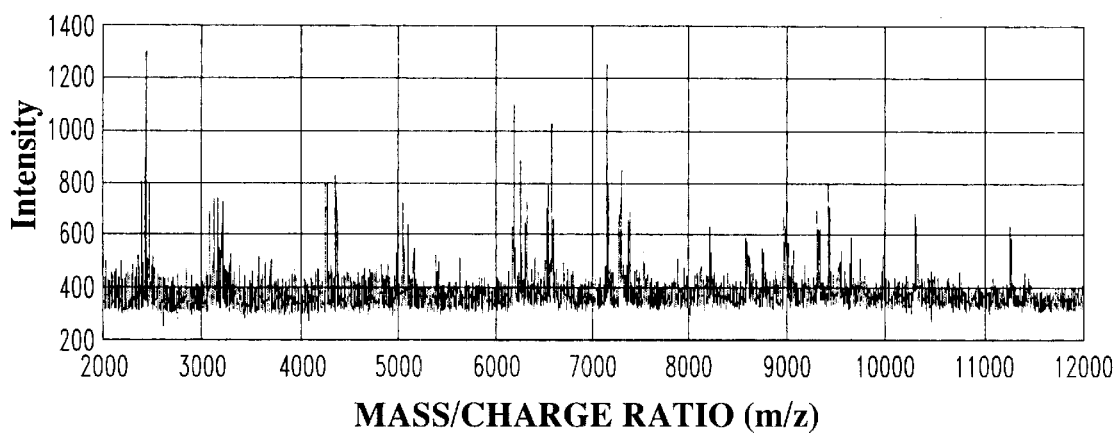
FIG. 5b is a MALDI-MS spectrum graph for a mixture of *E. coli* and *S. alga,* as is known in the art.

An exemplary application of the one-stage model described above will now be presented in relation to experimental data and compared with a more traditional process control approach. Examples of the data to be analyzed are shown in FIGS. 5a and 5b, which illustrate typical MALDI-MS spectra. FIG. 5a plots the spectrum for a pure vegetative whole cell *Escherichia coli* culture, while FIG. 5b plots a typical spectrum for an approximately 1:1 mixture of *E. coli* and *Shewanella alga*. In this comparison, 49 MALDI-MS spectra were used. The first 29 spectra contain only *E. coli* cells, while the last 20 contain a mixture of *E. coli* and *S. alga*. For both process control methods, the first 29 spectra were used in model construction to set the parameters of the algorithms. The last 20 spectra were used as a test set to determine if the algorithms could effectively identify a contaminated culture containing a mixture of organisms.

Figure 6A:
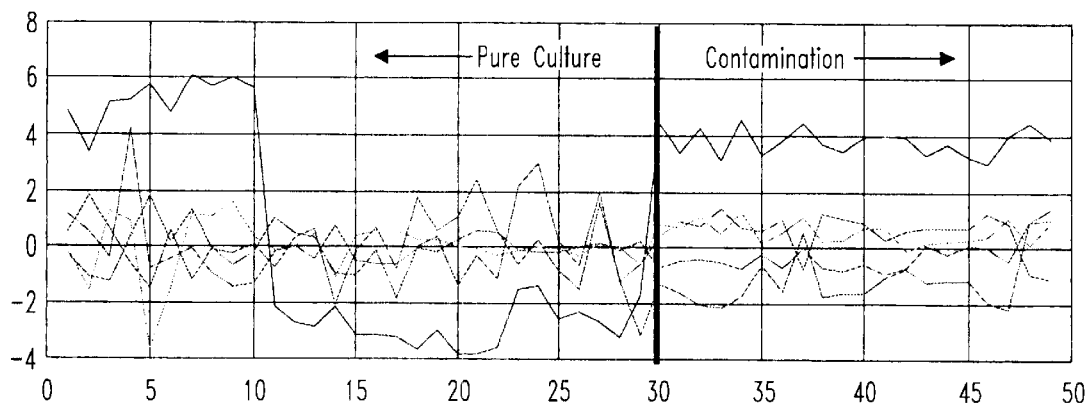
FIG. 6a is a graph of principal component scores for a series of indexed data sets corresponding to a sample, as is known in the art.
Figure 6B:
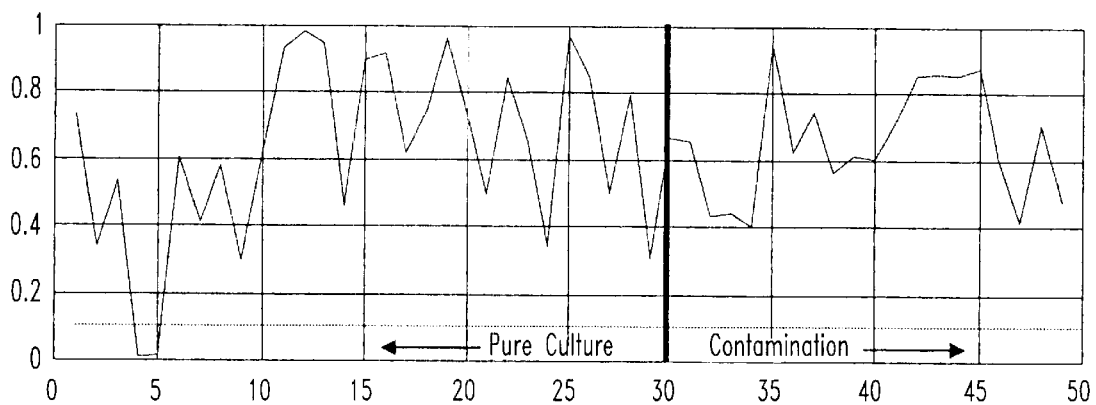
FIG. 6b is a graph of the $T^2$ test statistic for the same series of data sets, as is known in the art.

FIGS. 6a–6b show the results of the algorithm proposed by Nijhuis, et al. (Nijhuis, A.; Jong, S. d.; Vandegiste, B. G. M.; *Chemometrics and Intelligent Laboratory Systems*, vol. 38, pages 51–62 (1997)) as applied to the data shown in FIGS. 5a and 5b. In this case, five principal components were used, and they explain 74.4% of the variation in the pure culture spectra. FIG. 6a shows the principal components used in the $T^2$ chart. FIG. 6b shows the output of the process control algorithm. The thick solid vertical line at spectrum 30 indicates the division between the pure culture samples and the contaminated samples. In FIG. 6b, the solid line at $T^2=0.1$ represents the threshold for an out-of-control decision. In particular, $T^2$ values above the threshold are deemed in-control, while $T^2$ values falling below the threshold are deemed out-of-control.

Figure 7A:
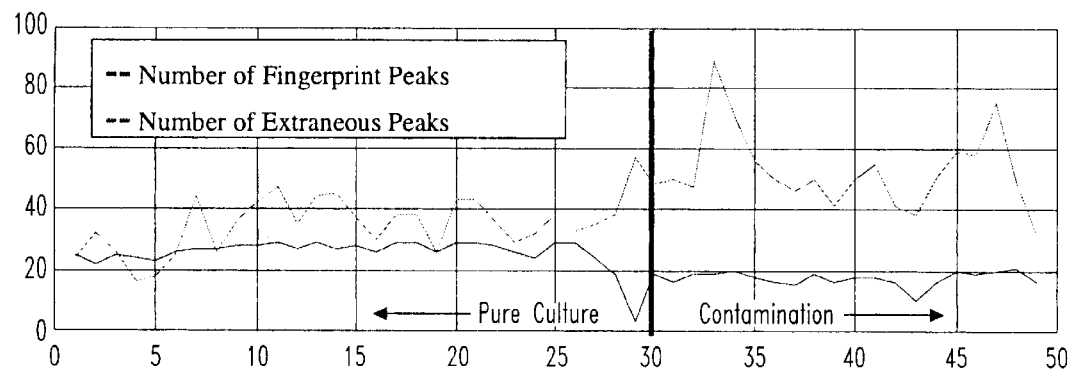
FIG. 7a is a graph of the number of fingerprint and extraneous peaks in consecutive data sets that characterize a sequence of cultures analyzed in one embodiment of the present invention.
Figure 7B:
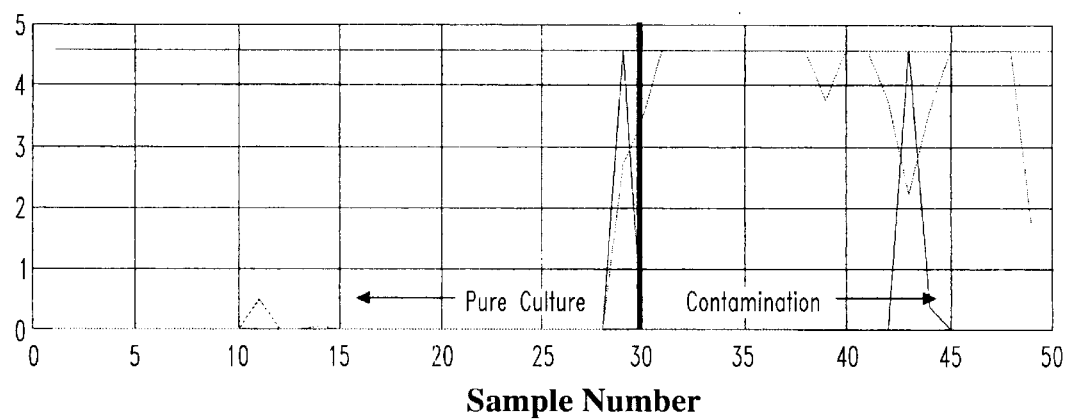
FIG. 7b is a graph of the CUSUM test statistic using the model described herein.

FIGS. 7a–7b display the results of the CUSUM algorithm based on a model according to the present invention. As in FIGS. 6a–6b, the thick vertical lines indicate the division between pure culture samples and contaminated samples. In FIG. 7b, the solid line at 4.6 represents the CUSUM threshold for the out-of-control decision. Samples where the CUSUM test statistic falls below the threshold are deemed in-control, while samples where the CUSUM test statistic falls on or above the threshold are deemed out-of-control.

FIGS. 6a–6b show that the traditional method fails to identify the culture contamination. The principal component scores do not significantly change from the pure culture to the mixture, and as a result, the process control technique does not detect any difference in the spectra. One possible reason for this is the high degree of variability in peak intensities typically observed in MALDI-MS spectra. Since principal components analysis is an intensity-based method, this high degree of variability translates into large variability in the scores for the pure culture data. As a result, when a change arises in the spectra, the principal components scores do not change significantly enough for the principal components algorithm to detect it.

On the other hand, FIGS. 7a–7b demonstrate that the method proposed here easily identifies the change in the MALDI spectra. This approach is based on the collection of peaks found in a sample, rather than the relative peak intensities or other characteristics of the peaks. Therefore, it is better suited to the problem of detecting extraneous peaks resulting from a contaminated culture.

Figure 9A:
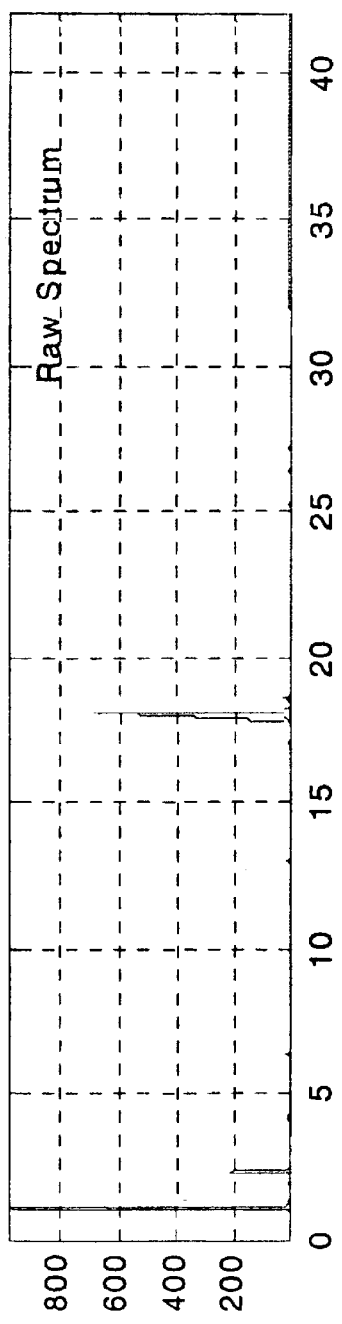
FIGS. 9a–9c are graphs of the raw spectrum, weighted variance, and peaks, respectively, of a test sample.
Figure 9B:
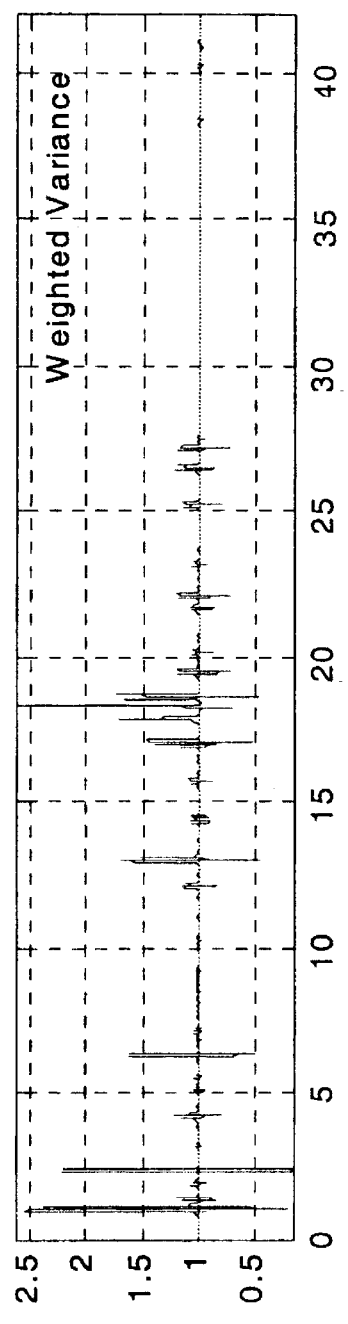
Figure 9C:
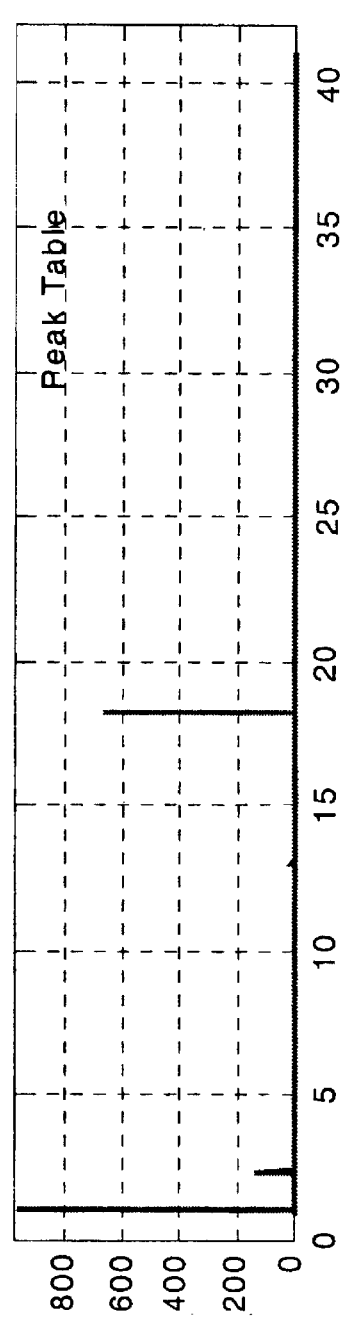

We illustrate a two-stage adaptation of the CUSUM method using gas chromatography data. The data consists of 25 gas chromatograms of unknown samples. Samples 1–10 came from a first lot. Samples 11–15 came from a second lot thought to be similar to the first lot. Samples 16–20 were thought to be slightly different from the first lot, and samples 21–25 were thought to be significantly different from the first lot. Each data set contained peak intensities at 15,750 retention times. The first lot was used as training data for the model. The raw chromatogram of sample 1 and its detected peaks are given in FIG. 8. For comparison, the chromatogram of sample 25 (which was not in the training data) and its detected peaks are shown in FIG. 9.

Figure 10A:
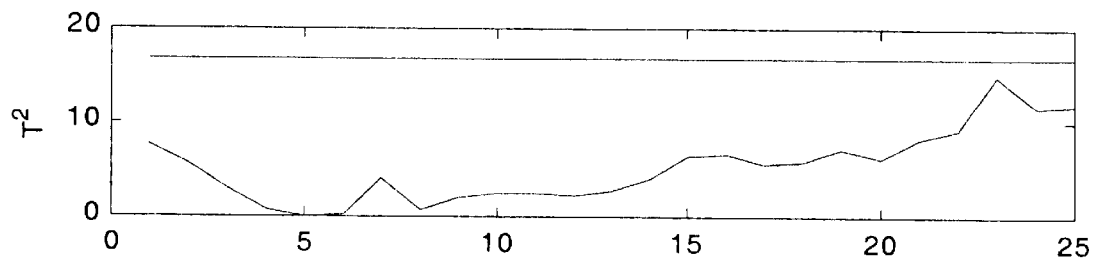
FIGS. 10a–10c are graphs of the results of a $T^2$ analysis with three principal components (as is known in the art), a $T^2$ analysis with four principal components (as is known in the art), and a CUSUM test according to the present invention, respectively, for a particular series of spectra.
Figure 10B:
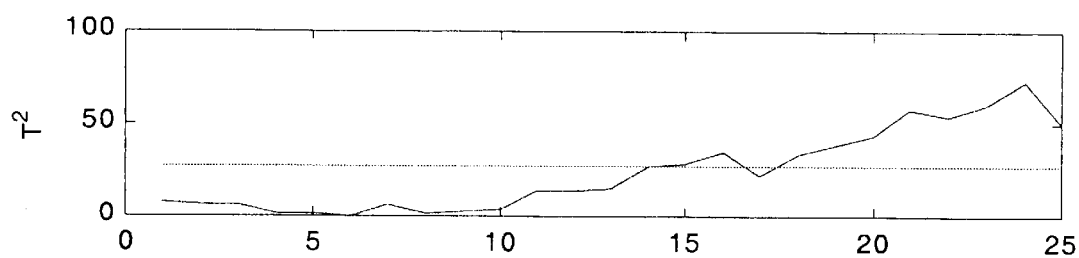
Figure 10C:
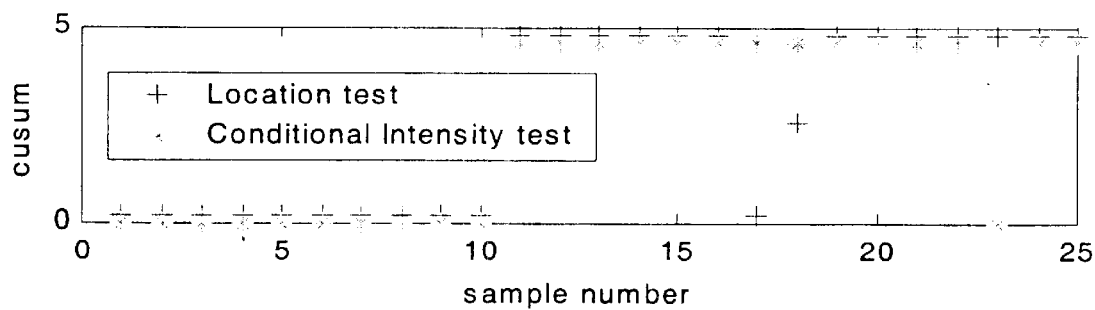

Results of the $T^2$ approach applied to the raw 25×15,750 data matrix are given in FIGS. 10a and 10b. In FIG. 10a, the $T^2$ statistic is computed using the first three principal component scores, which explain 97% of the variance in the training data. According to this test, none of the chromatograms deviate from the standard lot. In FIG. 10b, the $T^2$ statistic is computed using the first four principal component scores, which explain 98% of the variance in the training data—a minor improvement over the three-principal-component solution. But this test (FIG. 10b) shows that all but one of the last ten samples deviate from the standard lot. Results of the one- and two-stage CUSUM tests according to the present invention are shown in FIG. 10c. Both the location test and the conditional intensity test are in relative agreement with the $T^2$ test for the last ten samples. However, both the location test and the conditional intensity test suggest that samples 11–25 deviate from the standard lot. Inspection of the peak tables (not shown, except for samples 1 and 25 in FIGS. 8 and 9, respectively) revealed peaks in samples 11–25 that are not present in the training samples.

In applying this method, it is recommended that more that ten samples be used in a training set, in order to obtain more precise estimates of reference peak characteristics for use in the null hypothesis. In addition, the method is sensitive to the selection of alternate hypothesis peak characteristics.

Each document to which this specification refers is incorporated by reference as if fully set forth herein.

What is claimed is:

1. A method of determining whether a sample matches a reference species, the method comprising:

selecting N indices $l_1, l_2, \ldots l_N$ of peaks in an indexed data set characterizing the reference species;

selecting a first set of probabilities $p_1, p_2, \ldots p_N$ that peaks will occur at indices $l_1, l_2, \ldots l_N$, respectively, of an indexed data set that characterizes the sample when the sample matches the reference species;

selecting a second set of probabilities $q_1, q_2, \ldots q_N$ that peaks will occur at indices $l_1, l_2, \ldots l_N$, respectively, of an indexed data set that characterizes the sample when the sample does not match the reference species;

choosing a threshold $K_c$;

obtaining an indexed observation data set $x_1, x_2, \ldots x_N$, where $x_j \in \{0, 1\}$ and $x_j=1$ if and only if a peak is present in the sample at $l_j$;

deciding that the sample matches the reference species if $\lambda \leq K_c$ where $$\lambda = \sum_{1 \leq j \leq N} \log\left(\frac{1-p_j}{1-q_j}\right) + \sum_{1 \leq j \leq N} x_j \log\left[\frac{p_j(1-q_j)}{q_j(1-p_j)}\right];$$

and deciding that the sample does not match the reference species if $\lambda > K_c$.

2. The method of claim 1, wherein $K_c$ is selected such that, given that the sample matches the reference species, $P\{\lambda > K_c\} \leq \alpha$ for a predetermined type I error probability $\alpha$.

3. The method of claim 1, wherein said selecting steps comprise iterative proportional scaling calculations.

4. The method of claim 1, wherein said selecting steps comprise iterative weighted least squares calculations.

5. The method of claim 1, wherein said selecting steps comprise application of a Lancaster model.

6. The method of claim 1, wherein said selecting steps comprise application of a latent class model.

7. A method of detelaring whether a sample matches a reference species, the method comprising:

selecting N indices $l_1, l_2, \ldots l_N$ of peaks in an indexed data set characterizing the reference species;

selecting a first set of probabilities $p_1, p_2, \ldots p_N$ that peaks will occur at indices $l_1, l_2, \ldots l_N$ of an indexed data set that characterizes the sample when the sample matches the reference species;

selecting a first set of probability density functions $g_i(y_i; \theta_i)$ that characterize a measurable feature $y_i$ of the peak at index $l_i$ given the presence of a peak at index $l_i$ of a data set that characterizes the sample when the sample matches the reference species;

selecting a second set of probabilities $q_1, q_2, \ldots q_N$ that peaks will occur at indices $l_1, l_2, \ldots l_N$ of an indexed data set that characterizes the sample when the sample does not match the reference species;

selecting a second set of probability density functions $g_i(y_i; \Omega_i)$ that characterize the measurable feature $y_i$ of the peak at index $l_i$ given the presence of a peak at index $l_i$ of a data set that characterizes the sample when the sample does not match the reference species;

selecting a threshold $K_c$;

obtaining an indexed observation data set $x_1, x_2, \ldots x_N$ where $x_i \in \{0, 1\}$ and $x_i = 1$ if and only if a peak is present in the sample at $l_i$;

obtaining a feature data set $y_1, y_2, \ldots y_N$; and deciding that the sample matches the reference species if $\lambda \leq K_c$ where $$\lambda = \sum_{i=1}^{N} \left[ \log \frac{1 - p_i}{1 - q_i} + x_i \left\{ \log \frac{p_i(1 - q_i)}{q_i(1 - p_i)} + \log \frac{g_i(y_i; \theta_i)}{g_i(y_i; \Omega_i)} \right\} \right];$$

and deciding that the sample does not match the reference species if $\lambda > K_c$.

8. The method of claim 7, wherein one or more $g_i(\cdot)$ is a lognormal density given by $$g_i(y_i; \theta_i) = g_i(y_i; \mu_i, \sigma_i^2) = \frac{1}{y_i \sqrt{2\pi\sigma^2}} \exp\left\{ -\frac{(\log y_i - \mu_i)^2}{2\sigma_i^2} \right\},$$

$y_i \geq 0$.

9. The method of claim 7, wherein one or more $g_i(\cdot)$ is a gamma density given by $$g_i(y_i; \theta_i) = g_i(y_i; \alpha_i, \beta_i) = \frac{1}{\Gamma_{\alpha_i} \beta_i^{\alpha_i}} y_i^{\alpha_i - 1} \exp(-y_i/\beta_i), \, y_i \geq 0.$$

10. The method of claim 7, wherein one or more $g_i(\cdot)$ is a Poisson density given by $$g_i(y_i; \theta_i) = \frac{\theta^{y_i} \exp(-\theta_i)}{y_i!}, \, y_i = 0, 1, 2, \ldots.$$

11. The method of claim 7, wherein the measurable feature is the intensity of the peak at index $l_i$.

12. The method of claim 7, wherein the measurable feature is the width of the peak at index $l_i$.

13. The method of claim 7, wherein the measurable feature is a quantification of the skew of the peak at index $l_i$.

14. A method, wherein the status of a process at any point t in time is characterized by an indexed observation data set $X_t = \{x_{1,t}, x_{2,t}, \ldots x_{N,t}\}$, where $x_{j,t} \in \{0, 1\}$ and $x_{j,t} = 1$ if and only if a peak is present at time t in the sample at index $l_j$, the method comprising:

selecting a first set of probabilities $p_1, p_2, \ldots p_N$ that peaks will occur at $x_{1,t}, x_{2,t}, \ldots x_{N,t}$, respectively, when the process is operating normally;

selecting a second set of probabilities $q_1, q_2, \ldots q_N$ that peaks will occur at $x_{1,t}, x_{2,t}, \ldots x_{N,t}$, respectively, when the process is not operating normally;

acquiring a sequence $X_1, X_2, \ldots X_T$ of indexed observation data sets;

intervening in the process when it is determined that $C_n$ equals or exceeds a predetermined value A, where $C_0 = 0$;

$C_n = S_n - \min_{1 \leq j \leq n} \{S_j\}$ for $n \geq 1$; and $$S_n = \sum_{1 \leq j \leq n} \log\left(\frac{1 - p_j}{1 - q_j}\right) + \sum_{1 \leq j \leq n} x_{j,t} \log\left[\frac{p_j(1 - q_j)}{q_j(1 - p_j)}\right].$$

15. The method of claim 14, wherein A is selected as a function of the desired false alarm rate for the test.

16. The method of claim 14, wherein said intervening comprises stopping the process.

17. A method, wherein the status of a process at any point t in time is characterized by
an indexed observation data set $X_t = \{x_{1,t}, x_{2,t}, \ldots x_{N,t}\}$, where $x_{j,t} \in \{0, 1\}$ and $x_{j,t} = 1$ if and only if a peak is present at time t in the sample at index $l_j$, and
a feature data set $Y_t = \{y_{1,t}, y_{2,t}, \ldots y_{N,t}\}$, where if $x_{j,t} = 0$, $y_{j,t} = 0$, and if $x_{j,t} = 1$, $y_{j,t}$ quantifies a feature of the peak at time t in the sample at index $l_j$, the method comprising:

selecting a first set of probabilities $p_1, p_2, \ldots p_N$ that peaks will occur at $x_{1,t}, x_{2,t}, \ldots x_{N,t}$, respectively, when the process is operating normally;

selecting a first set of probability density functions $g_i(y_i; \theta_i)$ that characterize a measurable feature $y_i$ of the peak at index $l_i$ given the presence of a peak at index $l_i$ of a data set that characterizes the process when it is operating normally;

selecting a second set of probabilities $q_1, q_2, \ldots q_N$ that peaks will occur at $x_{1,t}, x_{2,t}, \ldots x_{N,t}$, respectively, when the process is not operating normally;

selecting a second set of probability density functions $g_i(y_i; \Omega_i)$ that characterize the measurable feature $y_i$ of the peak at index $l_i$ given the presence of a peak at index $l_i$ of a data set that characterizes the process when it is operating normally;

acquiring a sequence $X_1, X_2, \ldots X_T$ of indexed observation data sets;

acquiring a sequence $Y_1, Y_2, \ldots Y_T$ of feature data sets;

intervening in the process when it is determined that $C_n$ equals or exceeds a predetermined value A, where $C_0 = 0$;

$C_n = S_n - \min_{1 \leq j \leq n} \{S_j\}$ for $n \geq 1$; and $$S_n = \sum_{i=1}^{N} \left[ \log \frac{1-p_i}{1-q_i} + x_i \left\{ \log \frac{p_i(1-q_i)}{q_i(1-p_i)} + \log \frac{g_i(y_i; \theta_i)}{g_i(y_i; \Omega_i)} \right\} \right].$$

18. The method of claim 17, wherein one or more $g_i(\cdot)$ is a lognormal density function given by $$g_i(y_i; \theta_i) = g_i(y_i; \mu_i, \sigma_i^2) = \frac{1}{y_i \sqrt{2\pi\sigma^2}} \exp\left\{ -\frac{(\log y_i - \mu_i)^2}{2\sigma_i^2} \right\},$$

$y_i \geq 0$.

19. The method of claim 17, wherein one or more $g_i(\cdot)$ is a gamma density given by $$g_i(y_i; \theta_i) = g_i(y_i; \alpha_i, \beta_i^2) = \frac{1}{\Gamma_{\alpha_i} \beta_i^{\alpha_i}} y_i^{\alpha_i - 1} \exp(-y_i / \beta_i), \ y_i \geq 0.$$

20. The method of claim 17, wherein one or more $g_i(\cdot)$ is a Poisson density given by $$g_i(y_i; \theta_i) = \frac{\theta^{y_i} \exp(-\theta_i)}{y_i!}, \ y_i = 0, 1, 2, \ldots.$$

21. The method of claim 17, wherein the measurable feature is the intensity of the peak at index $l_j$.

22. The method of claim 17, wherein the measurable feature is the width of the peak at index $l_j$.

23. The method of claim 17, wherein the measurable feature is a quantification of the skew of the peak at index $l_j$.

24. The method of claim 17, wherein A is selected as a function of the desired false alarm rate for the test.

25. The method of claim 17, wherein said intervening comprises stopping the process.

26. A system for analyzing a sample in comparison with a reference species, comprising:
   a processor;
   a memory storing data indicative of:
      probabilities $p_1, p_2, \ldots p_N$ that peaks will occur at indices $l_1, l_2, \ldots l_N$ of an indexed data set that characterizes the sample when the sample matches the reference species;
      probabilities $q_1, q_2, \ldots q_N$ that peaks will occur at indices $l_1, l_2, \ldots l_N$ of an indexed data set that characterizes the sample when the sample does not match the reference species;
      a threshold value; and
      an indexed sample data set $x_1, x_2, \ldots x_N$ characterizing the sample, wherein each $x_i$ is a binary value that indicates whether or not a peak is present at index $l_i$; and
   a computer-readable medium encoded with programming instructions executable by said processor to:
      calculate a log-likelihood ratio $\lambda$, where $$\lambda = \sum_{1 \leq j \leq N} \log\left(\frac{1-p}{1-q_j}\right) + \sum_{1 \leq j \leq N} x_j \log\left[\frac{p_j(1-q_j)}{q_j(1-p_j)}\right];$$

generate a first signal when $\lambda$ is less than said threshold value; and
   generate a second signal when $\lambda$ is greater than said threshold value.

27. A method of performing discriminant analysis, the method comprising:
   selecting N indices $l_1, l_2, \ldots l_N$ of peaks in an indexed data set characterizing a first reference species or a second reference species;
   selecting a first set of probabilities $p_{1,1}, p_{2,1}, \ldots p_{N,1}$ that peaks will occur at indices $l_1, l_2, \ldots l_N$, respectively, of an indexed data set that characterizes the sample when the sample matches the first reference species;
   selecting a second set of probabilities $p_{1,2}, p_{2,2}, \ldots p_{N,2}$ that peaks will occur at indices $l_1, l_2, \ldots l_N$, respectively, of an indexed data set that characterizes the sample when the sample matches the second reference species;
   selecting a third set of probabilities $q_{1,1}, q_{2,1}, \ldots q_{N,1}$ that peaks will occur at indices $l_1, l_2, \ldots l_N$, respectively, of an indexed data set that characterizes the sample when the sample matches a second reference species;
   selecting a fourth set of probabilities $q_{1,2}, q_{2,2}, \ldots q_{N,2}$ that peaks will occur at indices $l_1, l_2, \ldots l_N$, respectively, of an indexed data set that characterizes the sample when the sample matches a second reference species;
   obtaining an indexed observation data set $x_1, x_2, \ldots x_N$, where $x_j \in \{0, 1\}$ and $x_j=1$ if and only if a peak is present in the sample at $l_j$;
   calculating $$\lambda_1 = \sum_{1 \leq j \leq N} \log\left(\frac{1-p_{j,1}}{1-q_{j,1}}\right) + \sum_{1 \leq j \leq N} x_j \log\left[\frac{p_{j,1}(1-q_{j,1})}{q_{j,1}(1-p_{j,1})}\right] \text{ and}$$

$$\lambda_2 = \sum_{1 \leq j \leq N} \log\left(\frac{1-p_{j,2}}{1-q_{j,2}}\right) + \sum_{1 \leq j \leq N} x_j \log\left[\frac{p_{j,2}(1-q_{j,2})}{q_{j,2}(1-p_{j,2})}\right]; \text{ and}$$

deciding that
      the sample matches the first reference species if $\lambda_1 \leq \lambda_2$; and
      the sample matches the second reference species if $\lambda_1 > \lambda_2$.

28. A method of performing a cluster analysis of M samples, comprising:
   selecting N indices $l_1, l_2, \ldots l_N$ of possible peak locations in indexed data sets characterizing the M samples;
   obtaining indexed data sets $X_i = \{x_{1,i}, x_{2,i}, \ldots x_{N,i}\}$: $i=1, 2, \ldots M$, each data set corresponding to a different sample, wherein $x_{j,i} = \{0, 1\}$ and $x_{j,i}=1$ if and only if a peak exists in the data set for sample i at index $l_j$; and
   defining P groups of samples by
      selecting a first array of probabilities $p_{k,i}$: $k=1, 2, \ldots P$; $i=1, 2, \ldots N$ that peaks will occur at indices $l_1, l_2, \ldots l_N$, respectively, of an indexed data set that characterizes a sample when the sample is in group k;
      selecting a second array of probabilities $q_{k,i}$: $k=1, 2, \ldots P$; $i=1, 2, \ldots N$ that peaks will occur at indices $l_1, l_2, \ldots l_N$, respectively, of an indexed data set that characterizes the sample when the sample is not in group k; and
      selecting $g_j \in \{1, 2, \ldots P\}$: $j=1, 2, \ldots M$, where sample j is in group $g_j$; wherein $p_{k,i}$, $q_{k,i}$, and $g_j$ are selected to maximize $$\lambda = \sum_{1 \leq j \leq M} \left\{ \sum_{1 \leq j \leq N} \left[ \log\left(\frac{1-p_i}{1-q_i}\right) + x_{i,j} \log\left[\frac{p_{k,i}(1-q_{k,i})}{q_{k,i}(1-p_{k,i})}\right] \right] \bigg| k = g_j \right\}.$$

29. The method of claim 28, wherein P is also selected to maximize $\lambda$.

* * * * *